US010590077B2

(12) United States Patent
Brnardic et al.

(10) Patent No.: US 10,590,077 B2
(45) Date of Patent: Mar. 17, 2020

(54) TRPV4 ANTAGONISTS

(71) Applicant: GlaxoSmithKline Intellectual Property (No.2) Limited, Brentford, Middlesex (GB)

(72) Inventors: Edward J. Brnardic, Collegeville, PA (US); Carl A. Brooks, Collegeville, PA (US); Brian W. Budzik, Collegeville, PA (US); Brian Griffin Lawhorn, Collegeville, PA (US); Jay M. Matthews, Collegeville, PA (US); John Jeffrey McAtee, Collegeville, PA (US); Joseph E. Pero, Collegeville, PA (US); David J. Behm, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/334,410

(22) PCT Filed: Sep. 20, 2017

(86) PCT No.: PCT/IB2017/055703
§ 371 (c)(1),
(2) Date: Mar. 19, 2019

(87) PCT Pub. No.: WO2018/055527
PCT Pub. Date: Mar. 29, 2018

(65) Prior Publication Data
US 2019/0202784 A1 Jul. 4, 2019

Related U.S. Application Data

(60) Provisional application No. 62/397,013, filed on Sep. 20, 2016, provisional application No. 62/482,307, filed on Apr. 6, 2017.

(51) Int. Cl.
| | | |
|---|---|---|
| A61K 31/40 | (2006.01) |
| A61K 31/695 | (2006.01) |
| A61K 31/407 | (2006.01) |
| A61K 31/501 | (2006.01) |
| A61K 31/4439 | (2006.01) |
| A61K 31/429 | (2006.01) |
| A61K 31/4155 | (2006.01) |
| A61K 31/427 | (2006.01) |
| A61K 31/4025 | (2006.01) |
| A61K 31/506 | (2006.01) |
| A61K 31/4245 | (2006.01) |
| A61K 31/424 | (2006.01) |
| A61K 31/5386 | (2006.01) |
| A61K 45/06 | (2006.01) |
| C07D 491/107 | (2006.01) |
| C07D 401/12 | (2006.01) |
| C07D 513/04 | (2006.01) |
| C07D 417/12 | (2006.01) |
| C07D 409/12 | (2006.01) |
| C07D 403/12 | (2006.01) |
| C07D 413/12 | (2006.01) |
| C07D 207/48 | (2006.01) |
| C07D 498/10 | (2006.01) |
| A61P 9/04 | (2006.01) |
| A61P 11/14 | (2006.01) |

(52) U.S. Cl.
CPC ............ C07D 207/48 (2013.01); A61K 31/40 (2013.01); A61K 31/4439 (2013.01); A61K 45/06 (2013.01); A61P 9/04 (2018.01); A61P 11/14 (2018.01); C07D 401/12 (2013.01)

(58) Field of Classification Search
CPC .... A61K 31/40; A61K 31/695; A61K 31/407; A61K 31/501; A61K 31/4439; A61K 31/429; A61K 31/4155; A61K 31/427; A61K 31/4025; A61K 31/506; A61K 31/4245; A61K 31/424; A61K 31/5386; A61K 45/06; C07D 491/107; C07D 401/12; C07D 513/04; C07D 417/12; C07D 409/12; C07D 403/12; C07D 413/12; C07D 207/48; C07D 498/10
See application file for complete search history.

(56) References Cited

U.S. PATENT DOCUMENTS

| | | |
|---|---|---|
| 6,417,219 B1 | 7/2002 | Natchus et al. |
| 2006/0155129 A1 | 7/2006 | Gharbaoui et al. |
| 2007/0142394 A1 | 6/2007 | Solomon et al. |
| 2008/0004287 A1 | 1/2008 | Ma et al. |
| 2008/0176861 A1 | 7/2008 | Guha et al. |
| 2016/0024049 A1 | 1/2016 | Koike et al. |

FOREIGN PATENT DOCUMENTS

| | | |
|---|---|---|
| AU | 2005237500 | 4/2005 |
| CA | 2263928 A1 | 8/1997 |
| CA | 2567343 A1 | 12/2005 |

(Continued)

OTHER PUBLICATIONS

Parsons et al., caplus an 1997:566283 (Year: 1997).*
Barraclough et al., Tetrahedron, 51(14), 4195-4212 (Year: 1995).*
Hinata et al.,https://www.ncbi.nlm.nih.gov/pubmed/29438227 (Year: 2018).*
Xu et al., Oncotarget, 7(25), 37622-37635 (Year: 2016).*
Belvisi et al., https://erj.ersjournals.com/content/50/2/1601357 (Year: 2017).*
Corwin et al., https://www.atsjournals.org/doi/abs/10.1164/ajrccm-conference.2016.193.1_MeetingAbstracts.A1358 (Year: 2016).*
Achanta et al., https://www.atsjournals.org/doi/pdf/10.1164/ajrccm-conference.2019.199.1_MeetingAbstracts.A1017 (Year: 2019).*

(Continued)

Primary Examiner — Sun Jae Yoo
(74) Attorney, Agent, or Firm — Wayne J. Dustman; Fang Qian

(57) ABSTRACT

The present invention relates to pyrrolidine sulfonamide analogs, pharmaceutical compositions containing them and their use as TRPV4 antagonists.

20 Claims, No Drawings

(56) References Cited

FOREIGN PATENT DOCUMENTS

| CA | 2891551 A1 | 5/2014 |
|---|---|---|
| CA | 2904393 A1 | 9/2014 |
| EP | 1760079 A1 | 3/2007 |
| WO | WO03/050154 A2 | 6/2003 |
| WO | WO2004/086865 A1 | 10/2004 |
| WO | WO2005/115983 A1 | 12/2005 |
| WO | WO2006005551 A1 | 1/2006 |
| WO | WO 2007/082262 A2 | 7/2007 |
| WO | WO2009091941 A1 | 7/2009 |
| WO | WO10008739 A2 | 1/2010 |
| WO | WO14140310 A1 | 9/2014 |
| WO | WO2016016370 A1 | 2/2016 |
| WO | WO 2018/055524 | 3/2018 |
| WO | WO 2018/055526 | 3/2018 |

OTHER PUBLICATIONS

Goyal et al., https://rd.springer.com/article/10.1007/s40256-018-00320-6 (Year: 2019).*
Abdulqawi R, et al., *Lancet.*, 385(9974):1198-1205 (2015).
Alessandri-Haber, et al., *J Neurosci*, 26: 3864-3874 (2006).
Alvarez, et al., *Circ. Res.*, 99:988-985 (2006).
Auer-Grumbach, et al., *Nat Genet.* PMID: 20037588 (2009).
Balakrishna, et al., *Am J Physiol Lung Cell Mol Physiol*, 307: L158-L172 (2014).
Basoglu OK, et al., *Chest.*, 148(2):430-435 (2015).
Bhargave, et al., *Am J Rhinol*, 22:7-12 (2008).
Bonvini, et al., *J Allergy Clin Immunol*, 138: 249-261 (2016).
Chen, et al., *J Biol Chem*, 291: 10252-10262 (2016).
Delany, et al., *Physiol. Genomics*, 4:165-174 (2001).
Deng, et al., Nat Genet PMID: 20037587 (2009).
Duan, et al., *Mol Genet Genomics*, 290: 1357-1365 (2015).
Earley, et al., *Circ Res* 97: 1270-1279 (2005).
Everaerts, et al., *Proc Natl Acad Sci U S A*, 107: 19084-19089 (2010).
Fan, et al., *J. Biol. Chem.*, 284:27884-27891 (2009).
Grant, et al., *J Physiol*, 578: 715-733 (2007).
Guler, et al., *J. Neurosci*, 22:6408-6414 (2002).
Hamanaka, et al., *Am J Physiol.*, 293: L923-L932 (2007).
Hilfiker, et al., *ACS Med Chem. Lett.*, 4: 293-296 (2013).
Jian, et al., *Am. J. Respir. Cell Mol. Biol.*, 38:386-392 (2008).
Jie, et al., *Front Cell Neurosci*, 9: 141 (2015).
Jo, et al., *Proc Natl Acad Sci U S A*, 113: 3885-3890 (2016).
Krakow, et al., *Am J Hum Genet*, 84: 307-315 (2009).
Landoure, et al., *Nat Genet.* PMID: 20037586 (2009).
Li, et al., *Front Cell Neurosci*, 7: 17 (2013).
Liedtke & Simon, *Am J Physiol*, 287: 269-271 (2004).
Masuyama, et al., *Cell Metab*, 8: 257-265 (2008).
McAlexander MA, et al., *J Pharmacol Exp Ther.*, 349(1):118-125 (2014).
Monaghan, et al., *PloS One*, 10: e0128359 (2015).
Morty, et al., *Am J Physiol Lung Cell Mol Physiol*, 307: L817-L821 (2014).
Muramatsu, et al., *J. Biol. Chem.*, 282: 32158-32167 (2007).
Parsons, et al., Synthesis of hydroxy pyrrolidines and piperidines via free-radical cyclisations, *Journal of the Chemical Society*, 1(4):651-660 (1998).
Rahaman, et al., *J Clin Invest*, 124: 5225-5238 (2014).
Rock, et al., *Nat Genet*, 40: 999-1003 (2008).
Skerratt, et al., Identification of false positives in 'HTS hits to lead': The application of Bayesian models in HTS triage to rapidly deliver a series of selective TRPV4 antagonists, *MEDCHEMCOMM*, 4(1):244-251 (2013).
Strotmann, et al., *Nat. Cell Biol.*, 2:695-702 (2000).
Thornelone, et al., *Sci. Transl. Med.*, 4:159ra148 (2012).
Todaka, et al., *J Biol Chem*, 279: 35133-35138 (2004).
Vergnolle, *Biochem Pharmacol*, 89: 157-161 (2014.).
Vincent, et al., *Biochem Biophys Res Commun*, 389: 490-494 (2009).
Vriens, et al., *Proc. Atl. Acad. Sci. USA*, 101:396-401 (2004).
Wegierski, et al., *J. Biol. Chem.*, 284:2923-2933 (2009).
Willette, et al., *J. Pharmacol. Exp. Ther.*, 325:466-474 (2008).
Ye, et al., *Cell*, 151: 96-110 (2012).
Yin, et al., *Am J Respir Cell Mol Biol*, 54: 370-83 (2016).
Zhu, et al., *Hum Mol Genetics*, 18: 2053-2062 (2009).

* cited by examiner

TRPV4 ANTAGONISTS

This application is a 371 of International Application No. PCT/162017/055703, filed 20 Sep. 2017, which claims priority to U.S. 62/397,013 filed 20 Sep. 2016 and U.S. 62/482,307 filed 6 Apr. 2016.

FIELD OF THE INVENTION

The present invention relates to pyrrolidine sulfonamide analogs, pharmaceutical compositions containing them and their use as TRPV4 antagonists.

BACKGROUND OF THE INVENTION

TRPV4 is a member of the Transient Receptor Potential (TRP) superfamily of cation channels and is activated by heat, demonstrating spontaneous activity at physiological temperatures (Guler et al., 2002. *J Neurosci* 22: 6408-6414). Consistent with its polymodal activation property TRPV4 is also activated by hypotonicity and physical cell stress/pressure (Strotmann et al., 2000. *Nat Cell Biol* 2: 695-702), through a mechanism involving phospholipase A2 activation, arachidonic acid and epoxyeicosatrienoic acid generation (Vriens et al., 2004. *Proc Natl Acad Sci USA* 101:396-401). In addition, amongst other mechanisms proposed, tyrosine kinase activity, as well as protein kinase A and C, may also regulate TRPV4 (Wegierski et al., 2009. *J Biol Chem.* 284: 2923-33; Fan et al., 2009. *J Biol Chem* 284: 27884-91).

Heart failure results in the decreased ability of the left ventricle to pump blood into the peripheral circulation as indicated by a reduced ejection fraction and/or left ventricular dilation. This increases the left ventricular end diastolic pressure resulting in enhanced pulmonary blood pressures. This places the septal barrier, which separates the circulatory aqueous environment and the alveolar airspaces of the lung, at risk.

Increased pulmonary pressure results in the flow of fluid from the pulmonary circulation into the alveolar space resulting in lung edema/congestion, as is observed in patients with congestive heart failure.

TRPV4 is expressed in the lung (Delany et al., 2001. *Physiol. Genomics* 4: 165-174) and its level of expression is up-regulated in individuals with congestive heart failure (Thorneloe et al., 2012. *Sci Transl Med* 4: 159ra148). TRPV4 has been shown to mediate $Ca^{2+}$ entry in isolated endothelial cells and in intact lungs (Jian et al., 2009. *Am J Respir Cell Mol Biol* 38: 386-92). Endothelial cells are responsible for forming the capillary vessels that mediate oxygen/carbon dioxide exchange and contribute to the septal barrier in the lung. Activation of TRPV4 channels results in contraction of endothelial cells in culture and cardiovascular collapse in vivo (Willette et al., 2008. *J Pharmacol Exp Ther* 325: 466-74), at least partially due to the enhanced filtration at the septal barrier evoking lung edema and hemorrage (Alvarez et al., 2006. *Circ Res* 99: 988-95). Indeed, filtration at the septal barrier is increased in response to increased vascular and/or airway pressures and this response is dependent on the activity of TRPV4 channels (Jian et al., 2008. *Am J Respir Cell Mol Biol* 38:386-92). Consistent with these observations, TRPV4 antagonists prevent and resolve pulmonary edema in heart failure models (Thorneloe et al., 2012. *Sci Transl Med* 4: 159ra148). Overall this suggests a clinical benefit of inhibiting TRPV4 function in the treatment of acute and/or chronic heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics,* 18: 2053-62) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis (Rahaman et al., 2014. *J Clin Invest* 124: 5225-38), cough (Bonvini et al., 2016 *J Allergy Clin Immunol* 138: 249-61) and asthma (Liedtke & Simon, 2004. *Am J Physiol* 287: 269-71). A potential clinical benefit for TRPV4 blockers in the treatment of sinusitis, as well as allergic and non-allergic rhinitis is also supported (Bhargave et al., 2008. *Am J Rhinol* 22:7-12).

TRPV4 has been shown to be involved in acute lung injury (ALI). Chemical activation of TRPV4 disrupts the alvelor septal blood barrier potentially leading to pulmonary edema (Alvarez et al, *Circ Res.* 2006 Oct. 27; 99(9):988-95). In animal models, TRPV4 antagonism attenuates lung damage induced by chemical agents and biological toxins such as HCl, chlorine gas, and platelet activating factor (Balakrishna et al., 2014. *Am J Physiol Lung Cell Mol Physiol* 307: L158-72; Morty et al., 2014. *Am J Physiol Lung Cell Mol Physiol* 307: L817-21; Yin et al., 2016. *Am J Respir Cell Mol Biol* 54: 370-83). In addition, TRPV4 is necessary in a process known to cause or worsen ALI in humans (Hamanaka et al, *Am J Physiol Lung Cell Mol Physiol.* 2007 October; 293(4):L923-32). Overall this suggests a clinical benefit of inhibiting TRPV4 function in the treatment of ARDS and ALI.

Furthermore, TRPV4 has in recent years been implicated in a number of other physiological/pathophysiological processes in which TRPV4 antagonists are likely to provide significant clinical benefit. These include various aspects of pain (Todaka et al., 2004. *J Biol Chem* 279: 35133-35138; Grant et al., 2007. *J Physiol* 578: 715-733; Alessandri-Haber et al., 2006. *J Neurosci* 26: 3864-3874), genetic motor neuron disorders (Auer-Grumbach et al., 2009. *Nat Genet.* PMID: 20037588; Deng et al., 2009. *Nat Genet* PMID: 20037587; Landoure et al., 2009. *Nat Genet.* PMID: 20037586), cardiovascular disease (Earley et al., 2005. *Circ Res* 97: 1270-9; Yang et al., 2006. *Am. J Physiol.* 290: L1267-L1276), bone related disorders [including osteoarthritis (Muramatsu et al., 2007. *J. Biol. Chem.* 282: 32158-67), genetic gain-of function mutations (Krakow et al., 2009. *Am J Hum Genet* 84: 307-15; Rock et al., 2008 *Nat Genet* 40: 999-1003) and osteoclast differentiation (Masuyama et al. 2008. *Cell Metab* 8: 257-65)], itch (Akiyama et al., 2016. *J Invest Dermatol* 136: 154-60; Chen et al., 2016. *J Biol Chem* 291: 10252-62), stroke and disorders associated with cerebral edema (Li et al., 2013. *Front Cell Neurosci* 7: 17; Jie et al., 2015. *Front Cell Neurosci* 9: 141), inflammatory bowel disorders (Vergnolle, 2014. *Biochem Pharmacol* 89: 157-61), various diseases of the eye including glaucoma and retinopathy (Monaghan et al., 2015. *PloS One* 10: e0128359; Jo et al., 2016. *Proc Natl Acad Sci USA* 113: 3885-90), and metabolic syndrome including obesity and diabetes (Ye et al., 2012. *Cell* 151: 96-110; Duan et al., 2015. *Mol Genet Genomics* 290: 1357-65).

Thornelone et al., 2012. *Sci Trans Med* 4:159ra148; Balakrishna et al., 2014 *Am J Physiol Lung Cell Mol Physiol.* 307:L158-L172; Hilfiker et al., 2013 *ACS Med. Chem. Lett.* 4: 293-296; Skerratt et al., 2013 Med. *Chem. Commun.* 4: 244-251; Everaerts et al., 2010, *Proc Natl Acad Sci USA* 107: 19084-19089; and Vincent et al., 2009 *Biochem Biophys Res Commun* 389: 490-494, describe antagonists of TRPV4.

Chronic cough is highly prevalent worldwide and is highly impactful on the quality of life for suffers, with typical cough rates of 10-50 coughs per hour, during waking hours. It is hypothesized that chronic cough reflects a state of neuronal hypersensitivity involving exaggerated spinal and cortical responses to afferent sensory signals in a manner similar to chronic pain. Activation of TRPV4 channels in vivo causes ATP release and triggers afferent sensory signals from the lung through binding of ATP to P2X3 channels, resulting in cough (Bonvini S J, et al., J Allergy Clin Immunol. 2016 July; 138(1):249-261.e12). ATP levels are increased in exhaled breath of patients with diseases associated with cough, for example COPD (Basoglu O K, et al., Chest. 2015 August; 148(2):430-5). Recently a P2X3 antagonist has demonstrated high level efficacy in reducing chronic cough and improving quality of life scores in a phase 2 clinical trial (Abdulqawi R, et al. Lancet. 2015 Mar. 28; 385(9974):1198-1205). These clinical data along with data from pre-clinical models suggests a role for TRPV4 receptors in generating cough. TRPV4 receptors are expressed in airway smooth muscle cells (McAlexander M A, et al., J Pharmacol Exp Ther. 2014 April; 349(1):118-25), in airway epithelial cells (Delany N S, et al., Physiol Genomics. 2001 Jan. 19; 4(3):165-74), and in sensory neurons in the lung, including Ad-fibers from airway specific afferent neurons (Bonvini S J, et al., J Allergy Clin Immunol. 2016 July; 138(1):249-261.e12). Taken together, these data suggest a potential therapeutic role for TRPV4 antagonists in cough; including acute cough, sub-acute cough and chronic cough.

SUMMARY OF THE INVENTION

In one aspect this invention provides for pyrrolidine sulfonamide compounds of Formula (I), pharmaceutically acceptable salts thereof, and pharmaceutical compositions containing them.

In a second aspect, this invention provides for the use of the compounds of Formula (I) as TRPV4 antagonists.

In another aspect, this invention provides for compounds of Formula (I) for use in therapy.

In another aspect, this invention provides for the use of the compounds of Formula (I) for treating conditions associated with TRPV4 imbalance.

In yet another aspect, this invention provides for a method of treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence, which method comprises administering to a subject, suitably a human subject, in need thereof a therapeutically effective amount of a compound of Formula (I) or a pharmaceutically acceptable salt thereof.

In yet another aspect, this invention provides for the use of the compounds of Formula (I), and pharmaceutically acceptable salts thereof, for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, acute, chronic and polycystic kidney disease, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

In yet another aspect, this invention provides for compounds of Formula (I), and pharmaceutically acceptable salts thereof, for use in the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, acute, chronic and polycystic kidney disease, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

In yet another aspect, this invention provides for the use of the compounds of Formula (I), and pharmaceutically acceptable salts thereof, in the manufacture of a medicament for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, acute, chronic and polycystic kidney disease, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

The TRPV4 antagonist may be administered alone or in conjunction with one or more other therapeutic agents, eg. agents selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blockers, aldosterone antagonists, inotropes, NSAIDS, nitric oxide donors, calcium channel modulators, muscarinic antagonists, steroidal anti-inflammatory drugs, bronchodilators, antihistamines, leukotriene antagonist, HMG-CoA reductase inhibitors, dual non-selective β-adrenoceptor and α1-adrenoceptor antagonists, type-5 phosphodiesterase inhibitors, and renin inhibitors.

Other aspects and advantages of the present invention are described further in the following detailed description of the preferred embodiments thereof.

DETAILED DESCRIPTION OF THE INVENTION

This invention relates to compounds of Formula (I) and to the use of compounds of Formula (I) in the methods of the invention:

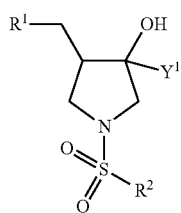

(I)

wherein:
$R^1$ is selected from:
  aryl,
  aryl substituted from 1 to 4 times by $R^a$,
  heteroaryl,
  heteroaryl substituted from 1 to 4 times by $R^a$,
  bicycloheteroaryl, and
  bicycloheteroaryl substituted from 1 to 4 times by $R^a$;
$R^2$ is selected from:
  aryl,
  aryl substituted from 1 to 4 times by $R^b$,
  heteroaryl,
  heteroaryl substituted from 1 to 4 times by $R^b$,
  bicycloheteroaryl, and
  bicycloheteroaryl substituted from 1 to 4 times by $R^b$, and $Y^1$ is selected from:
  $C_{1-6}$alkyl, and
  $C_{1-6}$alkyl substituted with from: 1 to 9 substitutents independently selected from:
    fluoro,
    chloro,
    bromo,
    iodo,
    —$OC_{1-6}$alkyl,
    —$OC_{1-6}$alkyl substituted with from 1 to 6 substituents independently selected from: fluoro, oxo, —OH, —COOH, —$NH_2$, and —CN,
    mercapto,
    —S(O)H,
    —$S(O)_2$H,
    oxo,
    hydroxy,
    amino,
    —$NHR^{x11}$,
      where $R^{x11}$ is selected from $C_{1-6}$alkyl, and $C_{1-6}$alkyl substituted with from 1 to 6 substituents independently selected from: fluoro, oxo, —OH, —COOH, —$NH_2$, —CN, —$OC_{1-5}$alkyl, —$OC_{1-5}$alkyl substituted from 1 to 6 times by fluoro and —$NH_2$,
    —$NR^{x12}R^{x13}$,
      where $R^{x12}$ and $R^{x13}$ are each independently selected from $C_{1-6}$alkyl, and $C_{1-6}$alkyl substituted with from 1 to 6 substituents independently selected from: fluoro, oxo, —OH, —COOH, —$NH_2$, and —CN,
    —C(O)OH,
    —$C(O)NH_2$,
    aryl,
    —Oaryl,
    heteroaryl,
    —Oheteroaryl,
    —$S(O)_2NH_2$,
    —$NHS(O)_2$H,
    nitro, and
    cyano, or
$Y^1$ is taken together with the adjacent —OH to form a heterocyclic ring selected from:
    morpholinyl,
    morpholinyl substituted by —$CH_3$, and
    oxazolidin-2-one;
each $R^a$ is independently selected from:
  fluoro,
  chloro,
  bromo,
  iodo,
  —OH,
  $C_{1-6}$alkyl,
  $C_{1-6}$alkyl substituted with from 1 to 5 substituents independently selected from: fluoro, chloro, bromo, iodo, $C_{1-4}$alkyloxy, —OH, $C_{1-4}$alkyl, phenyl, oxo, —COOH, —$NO_2$, —$NH_2$ and —CN,
  cyano,
  —$OC_{1-6}$alkyl,
  —$OC_{1-6}$alkyl substituted with from 1 to 5 substituents independently selected from: fluoro, chloro, bromo, iodo, $C_{1-4}$alkyloxy, —OH, $C_{1-4}$alkyl, phenyl, oxo, —COOH, —$NO_2$, —$NH_2$ and —CN,
  —Ophenyl,
  —$C(O)OC_{1-6}$alkyl,
  —$C(O)OC_{1-6}$alkyl substituted 1 to 5 times by fluoro, and
  —Ocycloalkyl; and each $R^b$ is independently selected from:
fluoro,
chloro,
bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkyloxy, —OH, $C_{1-4}$alkyl, phenyl, oxo, —COOH, —NO$_2$, —NH$_2$ and —CN,
cyano,
—OC$_{1-6}$alkyl,
—OC$_{1-6}$alkyl substituted with from 1 to 5 substituents independently selected from: fluoro, chloro, bromo, iodo, $C_{1-4}$alkyloxy, —OH, $C_{1-4}$alkyl, phenyl, oxo, —COOH, —NO$_2$, —NH$_2$ and —CN,
phenyl,
—C≡C—Si(CH$_3$)$_3$, and
—C≡C-cycloalkyl;
or a pharmaceutically acceptable salt thereof.

Suitably, in the compounds of Formula (I), $R^1$ is selected from:
aryl,
aryl substituted from 1 to 4 times by $R^a$,
heteroaryl,
heteroaryl substituted from 1 to 4 times by $R^a$,
bicycloheteroaryl, and
bicycloheteroaryl substituted from 1 to 4 times by $R^a$.

Suitably, in the compounds of Formula (I), $R^2$ is selected from:
aryl,
aryl substituted from 1 to 4 times by $R^b$,
heteroaryl,
heteroaryl substituted from 1 to 4 times by $R^b$,
bicycloheteroaryl, and
bicycloheteroaryl substituted from 1 to 4 times by $R^b$.

Suitably, in the compounds of Formula (I), $Y^1$ is selected from:
$C_{1-6}$alkyl, and
$C_{1-6}$alkyl substituted with from: 1 to 9 substitutents independently selected from:
fluoro,
chloro,
bromo,
iodo,
—OC$_{1-6}$alkyl,
—OC$_{1-6}$alkyl substituted with from 1 to 6 substituents independently selected from: fluoro, oxo, —OH, —COOH, —NH$_2$, and —CN,
mercapto,
—S(O)H,
—S(O)$_2$H,
oxo,
hydroxy,
amino,
—NHR$^{x11}$,
where $R^{x11}$ is selected from $C_{1-6}$alkyl, and $C_{1-6}$alkyl substituted with from 1 to 6 substituents independently selected from: fluoro, oxo, —OH, —COOH, —NH$_2$, —CN, —OC$_{1-5}$alkyl, —OC$_{1-5}$alkyl substituted from 1 to 6 times by fluoro and —NH$_2$,
—NR$^{x12}$R$^{x13}$,
where $R^{x12}$ and $R^{x13}$ are each independently selected from $C_{1-6}$alkyl, and $C_{1-6}$alkyl substituted with from 1 to 6 substituents independently selected from: fluoro, oxo, —OH, —COOH, —NH$_2$, and —CN,
—C(O)OH,
—C(O)NH$_2$,
aryl,
—Oaryl,
heteroaryl,
—Oheteroaryl,
—S(O)$_2$NH$_2$,
—NHS(O)$_2$H,
nitro, and
cyano, or
$Y^1$ is taken together with the adjacent —OH to form a heterocyclic ring selected from:
morpholinyl,
morpholinyl substituted by —CH$_3$, and
oxazolidin-2-one.

Included in the compounds of Formula (I) are compounds of Formula (II):

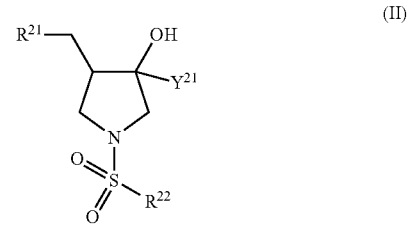

wherein:
$R^{21}$ is selected from:
aryl,
aryl substituted from 1 to 3 times by $R^{a2}$,
heteroaryl, and
heteroaryl substituted from 1 to 3 times by $R^{a2}$,
$R^{22}$ is selected from:
aryl,
aryl substituted from 1 to 3 times by $R^{b2}$, heteroaryl, and
heteroaryl substituted from 1 to 3 times by $R^{b2}$, and
$Y^{21}$ is selected from:
$C_{1-6}$alkyl, and
$C_{1-6}$alkyl substituted with from: 1 to 9 substitutents independently selected from:
fluoro,
chloro,
bromo,
—OC$_{1-6}$alkyl,
—OC$_{1-6}$alkyl substituted with from 1 to 6 substituents independently selected from: fluoro, oxo, —OH, —COOH, —NH$_2$, and —CN,
mercapto,
—S(O)H,
—S(O)$_2$H,
oxo,
hydroxy,
amino,
—NHR$^{x21}$,
where $R^{x21}$ is selected from $C_{1-5}$alkyl, and $C_{1-5}$alkyl substituted with from 1 to 6 substituents independently selected from: fluoro, oxo, —OH, —COOH, —NH$_2$, and —CN,
—C(O)OH,
—C(O)NH$_2$,
—S(O)$_2$NH$_2$, —NHS(O)$_2$H,
nitro, and
cyano;
each R$^{a2}$ is independently selected from:
fluoro,
chloro,
bromo,
—OH,
C$_{1-6}$alkyl,
C$_{1-6}$alkyl substituted with from 1 to 5 substituents independently selected from: fluoro, chloro, bromo, iodo, C$_{1-4}$alkyloxy, —OH, C$_{1-4}$alkyl, phenyl, oxo, —COOH, —NO$_2$, —NH$_2$ and —CN,
cyano,
—OC$_{1-6}$alkyl,
—OC$_{1-6}$alkyl substituted with from 1 to 5 substituents independently selected from: fluoro, chloro, bromo, iodo, C$_{1-4}$alkyloxy, —OH, C$_{1-4}$alkyl, phenyl, oxo, —COOH, —NO$_2$, —NH$_2$ and —CN,
—Ophenyl,
—C(O)OC$_{1-6}$alkyl,
—C(O)OC$_{1-6}$alkyl substituted 1 to 5 times by fluoro, and
—Ocycloalkyl; and
each R$^{b2}$ is independently selected from:
fluoro,
chloro,
bromo,
—OH,
C$_{1-6}$alkyl,
C$_{1-6}$alkyl substituted with from 1 to 5 substituents independently selected from: fluoro, chloro, bromo, iodo, C$_{1-4}$alkyloxy, —OH, C$_{1-4}$alkyl, phenyl, oxo, —COOH, —NO$_2$, —NH$_2$ and —CN,
cyano,
—OC$_{1-6}$alkyl,
—OC$_{1-6}$alkyl substituted with from 1 to 5 substituents independently selected from: fluoro, chloro, bromo, iodo, C$_{1-4}$alkyloxy, —OH, C$_{1-4}$alkyl, phenyl, oxo, —COOH, —NO$_2$, —NH$_2$ and —CN,
and
phenyl;
or a pharmaceutically acceptable salt thereof.
Suitably, in the compounds of Formula (II), R$^{21}$ is selected from:
aryl,
aryl substituted from 1 to 3 times by R$^{a2}$,
heteroaryl, and
heteroaryl substituted from 1 to 3 times by R$^{a2}$.
Suitably, in the compounds of Formula (II), R$^{22}$ is selected from:
aryl,
aryl substituted from 1 to 3 times by R$^{b2}$,
heteroaryl, and
heteroaryl substituted from 1 to 3 times by R$^{b2}$.
Suitably, in the compounds of Formula (II), Y$^{21}$ is selected from:
C$_{1-6}$alkyl, and
C$_{1-6}$alkyl substituted with from: 1 to 9 substituents independently selected from:
fluoro,
chloro,
bromo,
—OC$_{1-6}$alkyl,
—OC$_{1-6}$alkyl substituted with from 1 to 6 substituents independently selected from: fluoro, oxo, —OH, —COOH, —NH$_2$, and —CN,
mercapto,
—S(O)H,
—S(O)$_2$H,
oxo,
hydroxy,
amino,
—NHR$^{x21}$,
where R$^{x21}$ is selected from C$_{1-5}$alkyl, and C$_{1-5}$alkyl substituted with from 1 to 6 substituents independently selected from: fluoro, oxo, —OH, —COOH, —NH$_2$, and —CN,
—C(O)OH,
—C(O)NH$_2$,
—S(O)$_2$NH$_2$,
—NHS(O)$_2$H,
nitro, and
cyano.
Included in the compounds of Formula (I) are compounds of Formula (III):

(III)

wherein:
R$^{31}$ is selected from:
phenyl,
phenyl substituted from 1 to 3 times by R$^{a3}$,
pyrimidine,
pyrimidine substituted from 1 to 3 times by R$^{a3}$,
pyridine, and
pyridine substituted from 1 to 3 times by R$^{a3}$;
R$^{32}$ is selected from:
phenyl,
phenyl substituted from 1 to 3 times by R$^{b3}$,
pyridine,
pyridine substituted from 1 to 3 times by R$^{b3}$,
pyrimidine,
pyrimidine substituted from 1 to 3 times by R$^{b3}$,
pyridazine, and
pyridazine substituted from 1 to 3 times by R$^{b3}$; and
Y$^{31}$ is selected from:
—CH$_2$OH,
—CH(OH)CH$_3$,
—CH(OH)CH$_2$CH$_3$,
—C(OH)(CH$_3$)$_2$,
—CH$_2$NH$_2$,
—CH$_2$NHR$^{x30}$, and
—CH(NH$_2$)CH$_3$;
where each R$^{x30}$ is independently selected from:
C$_{1-6}$alkyl, and C$_{1-6}$alkyl substituted with from 1 to 6 substituents independently selected from: fluoro, oxo, —OH, —COOH, —NH$_2$, and —CN;
each R$^{a3}$ is independently selected from:
fluoro,
chloro,
bromo,
—OH,
C$_{1-6}$alkyl,
cyano,
—CF$_3$, $C_{1-5}$alkyl$CF_3$,
—$CHF_2$,
—$CH_2F$,
—$OC_{1-5}$alkyl,
—$OCF_3$,
$O_{1-4}$alkyl$CF_3$,
$C_{1-4}$alkylCN,
—C(O)O$C_{1-3}$alkyl,
—C(O)OH, and
—Ocycloalkyl; and
each $R^{b}3$ is independently selected from:
  fluoro,
  chloro,
  bromo,
  —OH,
  $C_{1-6}$alkyl,
  cyano,
  —$CF_3$,
  —$C_{1-4}$alkyl$CF_3$,
  —$CHF_2$,
  —$CH_2F$,
  —$OC_{1-3}$alkyl,
  —$OCF_3$,
  —$O_{1-4}$alkyl$CF_3$,
  —C(O)$CH_3$, and
  —$OCHF_2$;
or a pharmaceutically acceptable salt thereof.
Suitably, in the compounds of Formula (III), $R^{31}$ is selected from:
  phenyl,
  phenyl substituted from 1 to 3 times by $R^{a3}$,
  pyrimidine,
  pyrimidine substituted from 1 to 3 times by $R^{a3}$,
  pyridine, and
  pyridine substituted from 1 to 3 times by $R^{a3}$.
Suitably, in the compounds of Formula (III), $R^{32}$ is selected from:
  phenyl,
  phenyl substituted from 1 to 3 times by $R^{b3}$,
  pyridine,
  pyridine substituted from 1 to 3 times by $R^{b3}$,
  pyrimidine,
  pyrimidine substituted from 1 to 3 times by $R^{b3}$,
  pyridazine, and
  pyridazine substituted from 1 to 3 times by $R^{b3}$.
Suitably, in the compounds of Formula (III), $Y^{31}$ is selected from:
  —$CH_2OH$,
  —CH(OH)$CH_3$,
  —CH(OH)$CH_2CH_3$,
  —C(OH)$(CH_3)_2$,
  —$CH_2NH_2$,
  —$CH_2NHR^{x30}$, and
  —CH$(NH_2)CH_3$;
    where each $R^{x30}$ is independently selected from:
      $C_{1-6}$alkyl, and $C_{1-6}$alkyl substituted with from 1 to 6 substituents independently selected from: fluoro, oxo, —OH, —COOH, —$NH_2$, and —CN.
Included in the compounds of Formula (I) are compounds of Formula (IV):

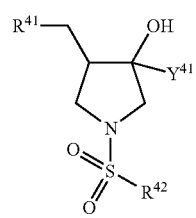

(IV)

wherein:
  $R^{41}$ is selected from:
    phenyl, and
    phenyl substituted from 1 to 3 times by $R^{a4}$;
  $R^{42}$ is selected from:
    phenyl,
    phenyl substituted from 1 to 3 times by $R^{b4}$,
    pyridine, and
    pyridine substituted from 1 to 3 times by $R^{b4}$; and
  $Y^{41}$ is selected from:
    —$CH_2OH$,
    —$CH_2NH_2$, and
    —$CH_2NHR^{x40}$;
      where each $R^{x40}$ is independently selected from:
        $C_{1-6}$alkyl, and $C_{1-6}$alkyl substituted with from 1 to 6 substituents independently selected from: fluoro, oxo, —OH, —COOH, —$NH_2$, and —CN;
  each $R^{a}4$ is independently selected from:
    fluoro,
    chloro,
    bromo,
    —OH,
    $C_{1-6}$alkyl,
    cyano,
    —$CF_3$,
    —$CHF_2$,
    —$CH_2F$,
    —$OC_{1-3}$alkyl,
    —$OCF_3$,
    —C(O)O$C_{1-3}$alkyl, and
    —C(O)OH, and
  each $R^{b}4$ is independently selected from:
    fluoro,
    chloro,
    —OH,
    $C_{1-6}$alkyl,
    cyano,
    —$CF_3$,
    —$CHF_2$,
    —$CH_2F$,
    —$OC_{1-3}$alkyl,
    —$OCF_3$,
    —C(O)$CH_3$, and
    —$OCHF_2$; and
or a pharmaceutically acceptable salt thereof.
Suitably, in the compounds of Formula (IV), $R^{41}$ is selected from:
  phenyl, and
  phenyl substituted from 1 to 3 times by $R^{a4}$.
Suitably, in the compounds of Formula (IV), $R^{42}$ is selected from:
  phenyl,
  phenyl substituted from 1 to 3 times by $R^{b4}$,
  pyridine, and
  pyridine substituted from 1 to 3 times by $R^{b4}$, Suitably, in the compounds of Formula (IV), $Y^{41}$ is selected from:
- —CH$_2$OH,
- —CH$_2$NH$_2$, and
- —CH$_2$NHR$^{x40}$;
    where each R$^{x40}$ is independently selected from: C$_{1-6}$alkyl, and C$_{1-6}$alkyl substituted with from 1 to 6 substituents independently selected from: fluoro, oxo, —OH, —COOH, —NH$_2$, and —CN.

Suitably, in the compounds of Formula (I), R$^1$ is phenyl independently substituted from 1 to 3 times by cyano and/or fluoro.

Suitably, in the compounds of Formula (I), R$^2$ is a substituted phenyl or a substituted pyridine.

Suitably, in the compounds of Formula (I), Y$^1$ is selected from: —CH$_2$OH, and —CH$_2$NH$_2$.

Representative compounds of the invention include the specific compounds described herein, e.g., the compounds of Formula (I) of the Examples, as well as any alternative stereoisomeric forms, free acid/base forms, salt forms, and alternative salt forms thereof (particularly pharmaceutically acceptable salt or alternative salt forms thereof), as applicable. Accordingly, in some embodiments the compound of the invention is a compound of Formula (I) selected from:

4-(((3S,4R)-1-((2,4-dichlorophenyl)sulfonyl)-4-hydroxy-4-(hydroxymethyl)pyrrolidin-3-yl)methyl)-2-fluorobenzonitrile;

4-(((3S,4R)-1-((2-chloro-4-(trifluoromethyl)phenyl)sulfonyl)-4-hydroxy-4-(hydroxymethyl)pyrrolidin-3-yl)methyl)benzonitrile;

4-(((3S,4R)-1-((5-chloropyridin-2-yl)sulfonyl)-4-hydroxy-4-(hydroxymethyl)pyrrolidin-3-yl)methyl)-3-(2,2,2-trifluoroethoxy)benzonitrile;

4-(((3S,4S)-1-((2,4-dichlorophenyl)sulfonyl)-4-hydroxy-4-(hydroxymethyl)pyrrolidin-3-yl)methyl)-2-fluorobenzonitrile;

4-(((3S,4R)-1-((2-cyano-4-(trifluoromethyl)phenyl)sulfonyl)-4-hydroxy-4-(hydroxymethyl)pyrrolidin-3-yl)methyl)-2-fluorobenzonitrile;

4-(((3S,4R)-1-((2-chloro-4-cyanophenyl)sulfonyl)-4-hydroxy-4-(hydroxymethyl)pyrrolidin-3-yl)methyl)-2-fluorobenzonitrile; and 4-(((3S,4S)-4-(aminomethyl)-1-((5-chloropyridin-2-yl)sulfonyl)-4-hydroxypyrrolidin-3-yl)methyl)-2-fluorobenzonitrile;

or a pharmaceutically acceptable salt thereof.

The skilled artisan will appreciate that salts, including pharmaceutically acceptable salts, of the compounds according to Formula (I) may be prepared. Indeed, in certain embodiments of the invention, salts including pharmaceutically-acceptable salts of the compounds according to Formula (I) may be preferred over the respective free or unsalted compound. Accordingly, the invention is further directed to salts, including pharmaceutically-acceptable salts, of the compounds according to Formula (I).

The salts, including pharmaceutically acceptable salts, of the compounds of the invention are readily prepared by those of skill in the art.

Typically, the salts of the present invention are pharmaceutically acceptable salts. Salts encompassed within the term "pharmaceutically acceptable salts" refer to non-toxic salts of the compounds of this invention.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidinyl, potassium, procaine, quinine, quinoline, sodium, strontium, t-butylamine, and zinc.

The compounds according to Formula I may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula I, or in any chemical structure illustrated herein, if not specified the structure is intended to encompass all individual stereoisomers and all mixtures thereof. Thus, compounds according to Formula I containing one or more chiral centers may be used as racemic mixtures, enantiomerically or diastereomerically enriched mixtures, or as enantiomerically or diastereomerically pure individual stereoisomers.

The compounds according to Formula (I) and pharmaceutically acceptable salts thereof may be in the form of isotopically-labelled compounds, wherein one or more atoms of Formula (I) are replaced by an atom having an atomic mass or mass number different from the atomic mass or mass number usually found in nature. Examples of such isotopes include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Isotopically-labelled compounds, for example those into which radioactive isotopes such as $^3$H or $^{14}$C are incorporated, are useful in drug and/or substrate tissue distribution assays. Tritium, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), both are useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds can generally be prepared by substituting a readily available isotopically labelled reagent for a non-isotopically labelled reagent.

The compounds according to Formula (I) may also contain double bonds or other centers of geometric asymmetry. Where the stereochemistry of a center of geometric asymmetry present in Formula (I), or in any chemical structure illustrated herein, is not specified, the structure is intended to encompass the trans (E) geometric isomer, the cis (Z) geometric isomer, and all mixtures thereof. Likewise, all tautomeric forms are also included in Formula (I) whether such tautomers exist in equilibrium or predominately in one form.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism ("polymorphs"). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may exist in solvated and unsolvated forms. As used herein, the term "solvate" refers to a complex of variable stoichiometry formed by a solute (in this invention, a compound of Formula (I) or a salt) and a solvent. Such solvents, for the purpose of the invention, may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice structures incorporated with water molecules are typically referred to as "hydrates". Hydrates include stoichiometric hydrates as well as compositions containing variable amounts of water.

It is also noted that the compounds of Formula (I) may form tautomers. 'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention.

While aspects for each variable have generally been listed above separately for each variable this invention includes those compounds in which several or each aspect in Formula (I) is selected from each of the aspects listed above. Therefore, this invention is intended to include all combinations of aspects for each variable.

Definitions

"Alkyl" refers to a hydrocarbon chain having the specified number of "member atoms". For example, $C_1$-$C_6$ alkyl refers to an alkyl group having from 1 to 6 member atoms. Alkyl groups may be saturated, unsaturated, straight or branched. Representative branched alkyl groups have one, two, or three branches. Alkyl includes but is not limited to: methyl, ethyl, ethylene, ethynyl, propyl (n-propyl and isopropyl), butene, butyl (n-butyl, isobutyl, and t-butyl), pentyl and hexyl.

"Alkoxy" refers to an —O-alkyl group wherein "alkyl" is as defined herein. For example, $C_1$-$C_4$alkoxy refers to an alkoxy group having from 1 to 4 carbon member atoms. Examples of such groups include but is not limited to: methoxy, ethoxy, propoxy, isopropoxy, butoxy, and t-butoxy.

"Aryl" refers to an aromatic hydrocarbon ring system. Aryl groups are monocyclic, bicyclic, and tricyclic ring systems having a total of five to fourteen ring member atoms, wherein at least one ring system is aromatic and wherein each ring in the system contains 3 to 7 member atoms, such as but no limited to: phenyl, dihydroindene, naphthalene, tetrahydronaphthalene and biphenyl. Suitably aryl is phenyl.

"Cycloalkyl", unless otherwise defined, refers to a saturated or unsaturated non aromatic hydrocarbon ring having from three to seven carbon atoms. Cycloalkyl groups are monocyclic ring systems. For example, $C_3$-$C_7$ cycloalkyl refers to a cycloalkyl group having from 3 to 7 member atoms. Examples of cycloalkyl as used herein include but is not limited to: cyclopropyl, cyclobutyl, cyclopentyl, cyclohexyl, cyclobutenyl, cyclopentenyl, cyclohexenyl and cycloheptyl. Suitably cycloalkyl is selected from: cyclopropyl, cyclopentyl and cyclohexyl.

"Heterocyclyl" refers to a saturated or unsaturated non-aromatic ring containing 4 to 12 member atoms, of which 1 to 11 are carbon atoms and from 1 to 6 are heteroatoms. Heterocycloalkyl groups containing more than one heteroatom may contain different heteroatoms. Heterocycloalkyl groups are monocyclic ring systems or a monocyclic ring fused with an aryl ring or to a heteroaryl ring having from 3 to 6 member atoms. In certain embodiments, heterocyclyl is saturated. In other embodiments, heterocyclyl is unsaturated but not aromatic. Heterocyclyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, oxetanyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, 1,3oxazolidin-2-one, hexahydro-1H-azepin, 4,5,6,7,tetrahydro-1H-benzimidazol, piperidinyl, 1,2,3,6-tetrahydro-pyridinyl and azetidinyl.

Suitably "Heterocyclyl" includes: pyrrolidinyl, oxazolidinyl, and morpholinyl,

"Heteroaryl" refers to a monocyclic aromatic 4 to 8 member ring containing from 1 to 7 carbon atoms and containing from 1 to 4 heteroatoms, provided that when the number of carbon atoms is 3, the aromatic ring contains at least two heteroatoms. Heteroaryl groups containing more than one heteroatom may contain different heteroatoms. Heteroaryl includes: pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl. Suitably, "heteroaryl" includes: pyrazolyl, pyrrolyl, isoxazolyl, pyridinyl, pyrimidinyl, pyridazinyl, and imidazolyl.

"Bicycloheteroaryl" refers to two fused rings, at least one of which is aromatic, containing from 1 to 6 heteroatoms as member atoms. Bicycloheteroaryl groups containing more than one heteroatom may contain different heteroatoms. Bicycloheteroaryl rings have from 6 to 11 member atoms. Bicycloheteroaryl includes: 1H-pyrrolo[3,2-c]pyridinyl, 1H-pyrazolo[4,3-c]pyridinyl, 1H-pyrazolo[3,4-d]pyrimidinyl, 1H-pyrrolo[2,3-d]pyrimidinyl, 7H-pyrrolo[2,3-d]pyrimidinyl, thieno[3,2-c]pyridinyl, thieno[2,3-d]pyrimidinyl, furo[2,3-c]pyridinyl, furo[2,3-d]pyrimidinyl, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzoxadiazole, imidazothiazole, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridinyl, furopyridinyl and napthyridinyl. Suitably "Bicycloheteroaryl" includes: benzoxadiazolyl and imidazothiazolyl.

"Heteroatom" refers to a nitrogen, sulphur or oxygen atom.

"Halogen" and "halo" refers to a fluorine, chlorine, bromine, or iodine atom.

As used herein, the term "mercapto" refers to the group —SH.

As used herein, the term "oxo" refers to the group =O.

As used herein, the term "hydroxy" refers to the group —OH.

As used herein, the term "amino" refers to the group —NH$_2$.

As used herein, the term "carboxy" refers to the group —C(O)OH.

As used herein, the term "cyano" refers to the group —CN.

As used herein, the term "nitro" refers to the group —NO$_2$.

Compound Preparation

The compounds according to Formula (I) are prepared using conventional organic synthetic methods. Suitable synthetic routes are depicted below in the following general reaction schemes. All of the starting materials are commercially available or are readily prepared from commercially available starting materials by those of skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

As used in the Schemes, "Ar" groups represent corresponding groups on any of Formulas I to IV. The compounds of Formulas I to IV can be prepared generally as described in the Schemes using appropriate substitutions for starting materials.

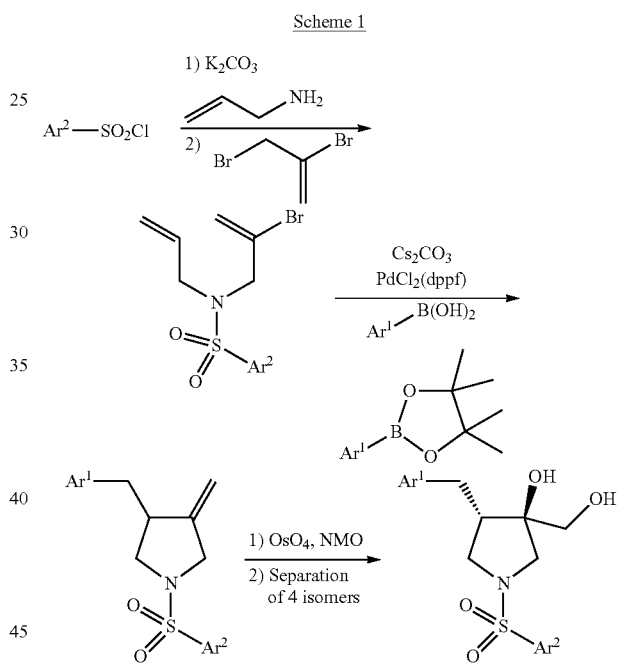

Scheme 1

Compounds of Formula (I) can be prepared by a multi-step sequence from substituted sulfonyl chlorides as shown in scheme 1. The appropriately substituted sulfonyl chloride can be treated with an alkyl amine using a base such as K$_2$CO$_3$ to give a secondary sulfonamide which can then be converted to the tertiary sulfonamide by substitution of an alkyl halide. Cyclization to the pyrrolidine with incorporation of the aromatic ring is then accomplished using a palladium catalyst such as PdCl$_2$(dppf), a substituted aryl boronic ester or acid, and a base such as Cs$_2$CO$_3$. The olefin intermediate can be dihydroxylated with catalytic OsO$_4$, using NMO as a cooxidant, to give the product of formula (I) as a mixture of 4 stereoisomers. Enantiopure trans-pyrrolidines can be obtained by separation of the mixture by chromatographic techniques such as supercritical fluid chromatography to give single isomers of compounds with Formula (I).

Scheme 2

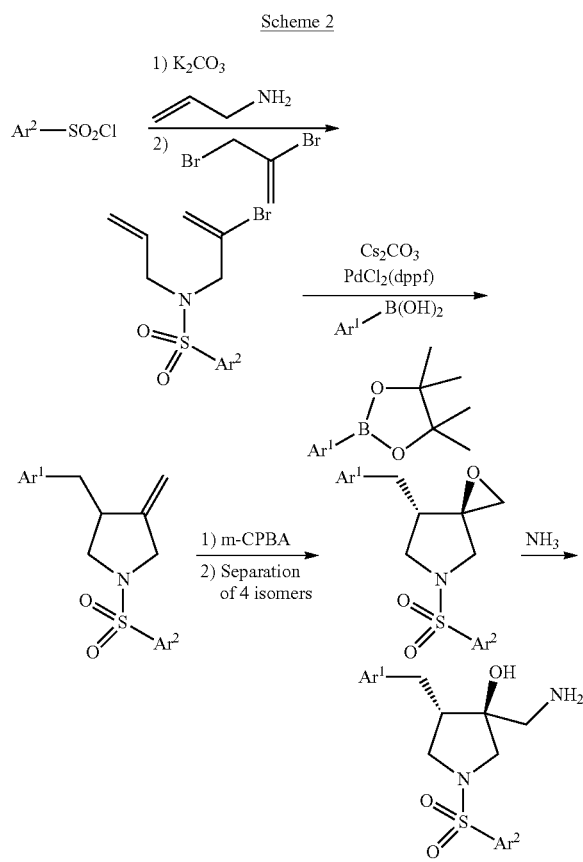

Compounds of Formula (I) can be prepared by a multi step sequence from substituted sulfonyl chlorides as shown in scheme 2. The appropriately substituted sulfonyl chloride can be treated with an alkyl amine in the presence of a base such as $K_2CO_3$ to give a secondary sulfonamide which can then be converted to the tertiary sulfonamide by substitution of an alkyl halide. Cyclization to the pyrrolidine with incorporation of the aromatic ring is then accomplished using a palladium catalyst such as $PdCl_2(dppf)$, a substituted aryl boronic ester or acid, and a base such as $Cs_2CO_3$. Epoxidation of the olefin intermediate is accomplished using m-CPBA to give the epoxide intermediate as a mixture of 4 stereoisomers. Enantiopure trans pyrrolidines can be obtained by separation of the mixture by chromatographic techniques such as supercritical fluid chromatography to give single isomers of compounds with Formula (I).

Biological Activity

As stated above, the compounds according to Formula I are TRPV4 antagonists. The biological activity of the compounds according to Formula I can be determined using any suitable assay for determining the activity of a candidate compound as a TRPV4 antagonist, as well as tissue and in vivo models. The biological activity of the compounds of Formula (I) are demonstrated by the following tests.

FLIPR Assay for hTRPV4 Expressed in BHK Cells:

TRPV4 channel activation results in an influx of divalent and monovalent cations including calcium. The resulting changes in intracellular calcium were monitored using a calcium specific fluorescent dye Fluo-4 (MDS Analytical Technologies). BHK/AC9 cells transduced with BacMam virus expressing the human TRPV4 gene at a MOI of 78 were plated in a 384 well poly-D lysine coated plate (15,000 cells/well in 50 μL culture medium containing DMEM/F12 with 15 mM HEPES, 10% FBS, 1% Penicillin-Streptomycin and 1% L-glutamine). Cells were incubated for 24 hours at 37° C. and 5% $CO_2$. Culture medium was then aspirated using a Tecan plate-washer and replaced with 20 μL/well of dye loading buffer: HBSS, 500 μM Brilliant Black (MDS Analytical Technologies), and 2 μM Fluo-4 AM. Dye loaded plates were then incubated in the dark at room temperature for 1~1.5 hours. 10 μL of test compounds diluted in HBSS (with 1.5 mM Calcium Chloride, 1.5 mM Magnesium Chloride and 10 mM HEPES, pH 7.4)+0.01% Chaps was added to each individual well of the plate, incubated for 10 min at room temperature in the dark and then 10 μL of agonist (N—((S)-1-(((R)-1-((2-cyanophenyl)sulfonyl)-3-oxoazepan-4-yl)amino)-4-methyl-1-oxopentan-2-yl)benzo[b]thiophene-2-carboxamide, (Thorneloe et al, Sci. Transl. Med. (2012), 4, 159ra148) (hereinafter: Agonist Compound) was added to have a final concentration equals to the agonist EC80. Calcium signals were measured using FLIPRTETRA (MDS Analytical Technologies) or FLIPR384 (MDS Analytical Technologies) and the inhibition of Agonist Compound-induced calcium signal by the test compound was determined.

All examples described herein possessed TRPV4 biological activity with $IC_{50}$ ranges from 0.1 nM-1 μM (see table below).

The compound of Example 1 was tested generally according to the above TRPV4 assay and in at least one set of experimental runs exhibited an average $IC_{50}$ (nM) value of 8.

The compound of Example 7 was tested generally according to the above TRPV4 assay and in at least one set of experimental runs exhibited an average $IC_{50}$ (nM) value of 10.

| EX # | $IC_{50}$ |
|---|---|
| 1 | +++ |
| 2 | ++ |
| 3 | ++ |
| 4 | ++ |
| 5 | +++ |
| 6 | +++ |
| 7 | +++ |

$IC_{50}$ Ranges: 0.1-10 nM (+++), >10-100 nM (++), >100-1000 nM (+).

Methods of Use

In yet another aspect, this invention provides a compound of Formula (I) or a pharmaceutically acceptable salt thereof in the treatment of a disease state selected from: atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, renal dysfunction, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence, through the administration of a compound of Formula (I) or a pharmaceutically acceptable salt thereof. Suitably the compounds of the invention are used in the treatment of congestive heart failure. Suitably the compounds of the invention are used in the treatment of acute lung injury. Suitably the compounds of the invention are used in the treatment of cerebral edema. Suitably the compounds of the invention are used in the treatment of heart failure. Suitably the compounds of the invention are used in the treatment of cough; including acute cough, sub-acute cough and chronic cough. Suitably the compounds of the invention are used in the treatment of acute respiratory distress syndrome. Accordingly, in another aspect the invention is directed to methods of treating such conditions.

The compounds of Formula (I) are tested for their ability to treat cough in in vivo in pre-clinical models in which cough is induced, for example the guinea pig model cited in Bonvini S J, et al., J Allergy Clin Immunol. 2016 July; 138(1):249-261.e12. The efficacy of compounds of Formula (I) are tested for their ability to treat cough; including acute cough, sub-acute cough and chronic cough, in people using the objective cough monitoring and specific quality of life instruments as cited in Abdulqawi R, et al. *Lancet.* 2015 Mar. 28; 385(9974):1198-1205.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The term "treating" and derivatives thereof refers to therapeutic therapy. Therapeutic therapy is appropriate to alleviate symptoms or to treat at early signs of disease or its progression.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" or "subject" refers to a human or other mammal.

In a further aspect, the invention provides for a compound of Formula (I) or a pharmaceutically acceptable salt thereof for use in the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, renal dysfunction, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence. Suitably the invention provides for a compound of Formula (I) or a pharmaceutically acceptable salt thereof for use in the treatment of congestive heart failure. Suitably the invention provides for a compound of Formula (I) or a pharmaceutically acceptable salt thereof for use in the treatment of acute lung injury. Suitably the invention provides for a compound of Formula (I) or a pharmaceutically acceptable salt thereof for use in the treatment cerebral edema. Suitably the invention provides for a compound of Formula (I) or a pharmaceutically acceptable salt thereof for use in the treatment of heart failure. Suitably the invention provides for a compound of Formula (I) or a pharmaceutically acceptable salt thereof for use in the treatment of cough; including acute cough, sub-acute cough and chronic cough. Suitably the invention provides for a compound of Formula (I) or a pharmaceutically acceptable salt thereof for use in the treatment of acute respiratory distress syndrome.

In another aspect, the invention provides for the use of a compound of Formula (I) or a pharmaceutically acceptable salt thereof in the manufacture of a medicament for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence. Suitably the invention provides for the use of a compound of Formula (I) or a pharmaceutically acceptable salt thereof in the manufacture of a medicament for the treatment of congestive heart failure. Suitably the invention provides for the use of a compound of Formula (I) or a pharmaceutically acceptable salt thereof in the manufacture of a medicament for the treatment of acute lung injury. Suitably the invention provides for the use of a compound of Formula (I) or a pharmaceutically acceptable salt thereof in the manufacture of a medicament for the treatment of cerebral edema. Suitably the invention provides for a compound of Formula (I) or a pharmaceutically acceptable salt thereof in the manufacture of a medicament for the treatment of heart failure. Suitably the invention provides for a compound of Formula (I) or a pharmaceutically acceptable salt thereof in the manufacture of a medicament for the treatment of cough; including acute cough, sub-acute cough and chronic cough. Suitably the invention provides for a compound of Formula (I) or a pharmaceutically acceptable salt thereof in the manufacture of a medicament for the treatment of acute respiratory distress syndrome.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration. Suitably the administration is oral. Suitably the administration is intravenous. Suitably the administration is by inhalation.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 1-500 mg once daily or BID per person.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

The compounds of Formula (I) and pharmaceutically acceptable salts thereof may be used in combination with one or more other agents which may be useful in the prevention or treatment of respiratory disease for example; antigen immunotherapy, antihistamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-methylpyridin-2-yl) methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

Suitably, for the treatment of asthma, COPD, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisilone. In one embodiment of the invention a corticosteroids for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a $\beta_2$-adrenoreceptor agonist, such as vilanterol, and an anticholinergic agent, such as, umeclidinium.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition.

For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* 17$^{th}$ ed. (Mack Publishing Company), *The Handbook of Pharmaceutical Additives* 1997 (Gower Publishing Limited), and *The Handbook of Pharmaceutical Excipients* 6$^{th}$ ed. (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* 17th ed. (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g., as in Turbuhaler, see EP 69715, or in the devices described in U.S. Pat. No. 6,321,747). An example of a unit-dose device is Rotahaler (see GB 2064336). In one embodiment, the Diskus inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery. Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art. The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose. Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds may be administered alone or in conjunction with one or more other therapeutic agents, said agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blockers, aldosterone antagonists, inotropes, NSAIDS, nitric oxide donors, calcium channel modulators, muscarinic antagonists, steroidal anti-inflammatory drugs, bronchodilators, antihistamines, leukotriene antagonists, HMG-CoA reductase inhibitors, dual non-selective β-adrenoceptor and α1-adrenoceptor antagonists, type-5 phosphodiesterase inhibitors, and renin inhibitors.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

LCMS data was generated using electrospray positive [ES+ve to give M+H$^+$ ion]equipped with a C18 column eluting with a gradient of 10%-100% acetonitrile/water containing either 0.05% or 0.1% TFA.

The naming program used is ACD Name Pro 6.02 or the naming functionality of Chem Draw Ultra 12.0.

The following abbreviations and terms have the indicated meanings throughout:

| Abbreviation | Meaning |
|---|---|
| aq | aqueous |
| BH$_3$ | borane |
| Boc | tert-butyloxycarbonyl |
| Boc$_2$O | di-tert-butyl dicarbonate |
| brine | saturated aqueous NaCl solution |
| t-BuOH | tert-butanol |
| Bz | benzoyl |
| CDI | carbonyldiimidazole |
| CH$_2$Cl$_2$ or DCM | methylene chloride |
| CH$_3$CN or MeCN | acetonitrile |
| Cs$_2$CO$_3$ | cesium carbonate |
| CuI | copper iodide |
| DCE | 1,2-dichloroethane |
| DEAD | diethylazodicarboxylate |
| DIAD | diisopropylazodicarboxylate |
| DME | dimethyl ether |
| DMF | N,N-dimethylformamide |
| DMSO | dimethylsulfoxide |
| dppf | 1,1'-bis(diphenylphosphino)ferrocene |
| ee | enantiomeric excess |
| ELSD | evaporative light scattering detector |
| Et$_3$N or TEA | triethylamine |
| EtOH | ethanol |
| Et$_2$O | diethyl ether |
| EtOAc | ethyl acetate |
| g | gram |
| Grubbs Catalyst, 2$^{nd}$ Generation | (1,3-Bis(2,4,6-trimethylphenyl)-2-imidazolidinylidene)dichloro(phenylmethylene)(tricyclohexylphosphine)ruthenium |
| h, hr | hour |
| HCl | hydrochloric acid |
| H$_2$SO$_4$ | sulfuric acid |
| i-PrOH or IPA | isopropanol |
| i-Pr$_2$NEt or DIPEA or DIEA | diisopropylethylamine |
| K$_2$CO$_3$ | potassium carbonate |
| t-BuOK | potassium tert-butoxide |
| KOH | potassium hydroxide |
| L | liter |
| LCMS | liquid chromatography-mass spectroscopy |
| M | molar |
| MC-OsO$_4$ | microencapsulated osmium tetraoxide |
| m-CPBA | metachloroperbenzoic acid |
| Me | methyl |
| MeMgBr | methyl magnesium bromide |
| MeOH or CH$_3$OH | methanol |
| MgSO$_4$ | magnesium sulfate |
| min | minute |
| mL | milliliter |
| mm | millimeter |
| mmol | millimole |
| MS | mass spectrum |
| MsCl | methanesulfonyl chloride |
| MTBE | methyl tert-butyl ether |
| N | normal |
| NaCl | sodium chloride |
| Na$_2$CO$_3$ | sodium carbonate |
| Na$_2$S$_2$O$_3$ | sodium thiosulfate |

-continued

| Abbreviation | Meaning |
|---|---|
| NaHCO$_3$ | sodium bicarbonate |
| NaHSO$_3$ | sodium bisulfite |
| NaN$_3$ | sodium azide |
| NaOH | sodium hydroxide |
| Na$_2$SO$_3$ | sodium sulfite |
| Na$_2$SO$_4$ | sodium sulfate |
| NCS | N-chlorosuccinimide |
| NH$_3$ | ammonia |
| NH$_4$Cl | ammonium chloride |
| NH$_4$OH | ammonium hydroxide |
| NMO | N-methylmorpholine N-oxide |
| NMR | nuclear magnetic resonance spectroscopy |
| OsO$_4$ | osmium tetraoxide |
| Pd(Cl)$_2$ | palladium dichloride |
| Pd$_2$(dba)$_3$ | tris(dibenzylideneacetone)dipalladium (0) |
| Pd(PPh$_3$)$_4$ | tetrakis(triphenylphosphine)palladium (0) |
| PMe$_3$ | trimethyl phosphine |
| PPh$_3$ | triphenyl phosphine |
| PS-PPh$_3$ | polymer supported triphenyl phosphine |
| RT or rt | room temperature |
| Sat'd | saturated |
| SFC | supercritical fluid chromatography |
| SiO$_2$ | silica gel |
| SM | starting material |
| TBAF | tetra-n-butylammonium fluoride |
| TFA | trifluoroacetic acid |
| THF | tetrahydrofuran |
| TLC | thin layer chromatography |
| V | volume |
| Zn(CN)$_2$ | zinc cyanide |

Example 1

4-(((3S,4R)-1-((2,4-dichlorophenyl)sulfonyl)-4-hydroxy-4-(hydroxymethyl)pyrrolidin-3-yl)methyl)-2-fluorobenzonitrile

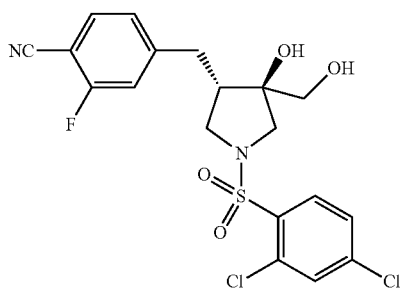 [SMILES: N#Cc1ccc(C[C@H]2CN(S(=O)(=O)c3ccc(Cl)cc3Cl)C[C@@]2(O)CO)cc1F]

Step 1: N-allyl-N-(2-bromoallyl)-2,4-dichlorobenzenesulfonamide

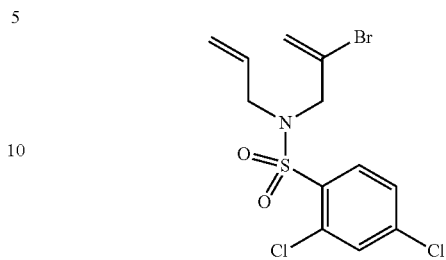

To a mixture of K$_2$CO$_3$ (25.3 g, 183 mmol) and 2,4-dichlorobenzene-1-sulfonyl chloride (15 g, 61 mmol) in dry DMF (122 mL) was added allylamine (5.0 mL, 67 mmol) and the reaction mixture was at rt. 2,3-Dibromoprop-1-ene (10.5 mL, 86 mmol) was added to the reaction and stirring continued at rt overnight. The reaction mixture was partitioned between water (1 L) and hexane (150 mL), the hexane layer removed and flash chromatographed (SiO$_2$) eluting with 0-10% EtOAc in hexanes. The product fractions were pooled and evaporated to give the title compound as a light yellow oil (15.5 g, 66% yield). MS (m/z) 383.7 (M+H$^+$).

Step 2: 4-((1-((2,4-dichlorophenyl)sulfonyl)-4-methylenepyrrolidin-3-yl)methyl)-2-fluorobenzonitrile

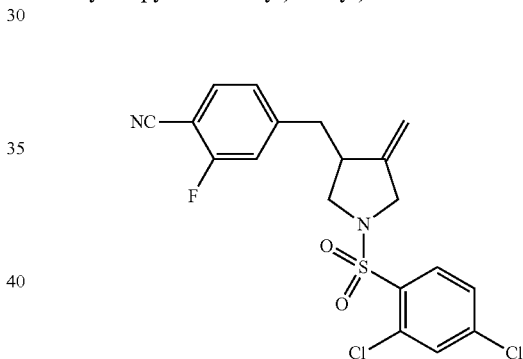

To a stirring suspension of N-allyl-N-(2-bromoallyl)-2,4-dichlorobenzenesulfonamide (5 g, 13 mmol, Cs$_2$CO$_3$ (12.7 g, 39.0 mmol), and 4-cyano-3-fluorophenyl)boronic acid (2.14 g, 13.0 mmol) in THF (45 mL) and water (20 mL) was added PdCl$_2$(dppf) (0.95 g, 1.3 mmol). The mixture was sparged with nitrogen and then heated at 60° C. for 30 min. The reaction mixture was cooled and extracted with EtOAc. The organic layer was dried over Na$_2$SO$_4$, filtered and concentrated under reduced pressure. The crude residue was purified by flash column chromatography (SiO$_2$) eluting with a gradient of 0-50% EtOAc in hexanes. The product fractions were pooled and concentrated under reduced pressure to give the title compound as an ivory solid (2.86 g, 52% yield). MS (m/z) 424.9 (M+H$^+$).

Step 3: 4-(((3S,4R)-1-((2,4-dichlorophenyl)sulfonyl)-4-hydroxy-4-(hydroxymethyl)pyrrolidin-3-yl)methyl)-2-fluorobenzonitrile To a solution of 4-((1-((2,4-dichlorophenyl)sulfonyl)-4-methylenepyrrolidin-3-yl)methyl)-2-fluorobenzonitrile (2.86 g, 6.72 mmol) in THF (45 mL) was added NMO (1.2 g, 10 mmol) followed by OsO$_4$ (2.5% in t-BuOH, 4.2 mL, 0.34 mmol) and the mixture stirred at rt overnight. The reaction was quenched with sat'd NaHSO₃ (aq) (25 mL), diluted with water and extracted with DCM. The organic layer was dried over Na₂SO₄, filtered, concentrated and purified by flash column chromatography (SiO₂) eluting with a gradient of 0-70% EtOAc in hexanes. The product fractions were pooled and concentrated to give a mixture of isomers, including the title compound, as a white solid (2.16 g). The isomer mixture can be separated into 4 individual components via preparative HPLC (Chiralpak IF, 30×250 mm) eluted with heptanes/EtOH (70/30) at a flowrate of 45 mL/min. After drying under high vac. at 40° C. for 1 h, the title compound was obtained as a white solid. 3S,4R-isomer:

86 mg, 3% yield, chiral HPLC: >99% ee, ¹H NMR (400 MHz, CDCl₃) δ: 8.00 (d, J=8.5 Hz, 1H), 7.53-7.60 (m, 2H), 7.40 (dd, J=8.5, 1.5 Hz, 1H), 7.05 (dd, J=19.8, 8.8 Hz, 2H), 3.75-3.85 (m, 2H), 3.71 (d, J=10.5 Hz, 1H), 3.53 (dd, J=9.9, 5.9 Hz, 1H), 3.40 (d, J=10.5 Hz, 1H), 3.20 (dd, J=9.9, 4.1 Hz, 1H), 3.03 (d, J=12.0 Hz, 1H), 2.84 (br s, 1H), 2.39-2.55 (m, 2H), 2.21 (br s, 1H). MS (m/z) 458.9 (M+H⁺).

The following compounds were prepared using procedures analogous to those described in Example 1 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 2 | 4-(((3S,4R)-1-((2-chloro-4-(trifluoromethyl)phenyl)sulfonyl)-4-hydroxy-4-(hydroxymethyl)pyrrolidin-3-yl)methyl)benzonitrile | 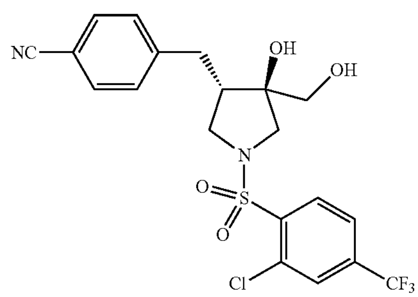 [SMILES: N#Cc1ccc(C[C@H]2CN(S(=O)(=O)c3ccc(C(F)(F)F)cc3Cl)C[C@@]2(O)CO)cc1] | 474.9 | ¹H NMR (400 MHz, CDCl₃) δ: 8.20 (d, J = 8.3 Hz, 1H), 7.82 (s, 1H), 7.66 (d, J = 8.3 Hz, 1H), 7.61 (d, J = 7.8 Hz, 2H), 7.23-7.31 (m, 2H), 3.71-3.89 (m, 3H), 3.51-3.64 (m, 1H), 3.42 (d, J = 10.8 Hz, 1H), 3.28 (dd, J = 9.8, 4.0 Hz, 1H), 3.03 (d, J = 12.5 Hz, 1H), 2.75 (br s, 1H), 2.40-2.56 (m, 2H), 2.04 (br s, 1H) |
| 3 | 4-(((3S,4R)-1-((5-chloropyridin-2-yl)sulfonyl)-4-hydroxy-4-(hydroxymethyl)pyrrolidin-3-yl)methyl)-3-(2,2,2-trifluoroethoxy)benzonitrile | 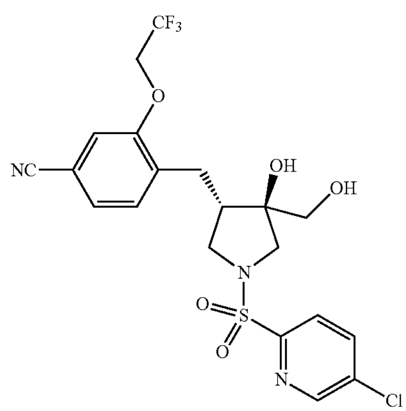 [SMILES: N#Cc1ccc(C[C@H]2CN(S(=O)(=O)c3ccc(Cl)cn3)C[C@@]2(O)CO)c(OCC(F)(F)F)c1] | 506.0 | ¹H NMR (400 MHz, DMSO-d₆) δ: 8.79 (d, J = 2.3 Hz, 1H), 8.22 (dd, J = 8.4, 2.4 Hz, 1H), 7.91 (d, J = 8.5 Hz, 1H), 7.60 (d, J = 1.0 Hz, 1H), 7.49 (dd, J = 7.8, 1.3 Hz, 1H), 7.29 (d, J = 7.8 Hz, 1H), 4.92 (s, 1H), 4.85 (q, J = 8.8 Hz, 2H), 4.77 (t, J = 5.1 Hz, 1H), 3.57 (d, J = 10.3 Hz, 1H), 3.37-3.42 (m, 3H), 3.06-3.19 (m, 2H), 2.87 (d, J = 10.0 Hz, 1H), 2.27-2.42 (m, 2H) |
| 4 | 4-(((3S,4S)-1-((2,4-dichlorophenyl)sulfonyl)-4-hydroxy-4-(hydroxymethyl)pyrrolidin-3-yl)methyl)-2-fluorobenzonitrile | 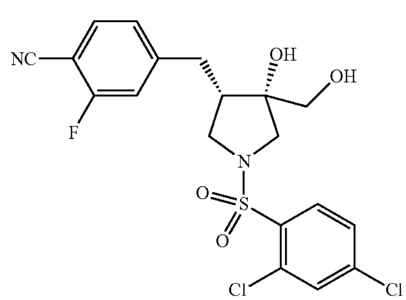 [SMILES: N#Cc1ccc(C[C@H]2CN(S(=O)(=O)c3ccc(Cl)cc3Cl)C[C@]2(O)CO)cc1F] | 458.9 | ¹H NMR (400 MHz, CDCl₃) 8.00 (d, J = 8.5 Hz, 1H), 7.50-7.61 (m, 2H), 7.40 (dd, J = 8.5, 1.5 Hz, 1H), 6.99-7.14 (m, 2H), 3.55-3.76 (m, 4H), 3.49 (t, J = 8.5 Hz, 1H), 3.31 (t, J = 9.7 Hz, 1H), 3.04 (dd, J = 14.1, 5.0 Hz, 1H), 2.66-2.83 (m, 2H), 2.34-2.51 (m, 1H), 2.14 (br s, 1H) |

| Ex. | Name | Structure | MS (m/z) (M + H⁺) | ¹H NMR |
|---|---|---|---|---|
| 5 | 4-(((3S,4R)-1-((2-cyano-4-(trifluoromethyl)phenyl)sulfonyl)-4-hydroxy-4-(hydroxymethyl)pyrrolidin-3-yl)methyl)-2-fluorobenzonitrile | 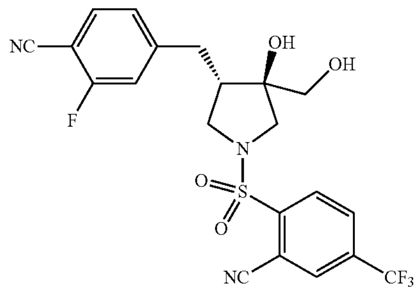 [SMILES: N#Cc1ccc(C[C@H]2CN(S(=O)(=O)c3ccc(C(F)(F)F)cc3C#N)C[C@@]2(O)CO)cc1F] | 484.1 | $^1$H NMR (400 MHz, DMSO-$d_6$) δ: 8.67 (s, 1H), 8.25-8.32 (m, 1H), 8.17-8.23 (m, 1H), 7.86 (t, J = 7.5 Hz, 1H), 7.32 (d, J = 10.5 Hz, 1H), 7.20 (dd, J = 7.9, 1.1 Hz, 1H), 5.10 (s, 1H), 4.83 (brs, 1H), 3.63 (d, J = 10.3 Hz, 1H), 3.36-3.44 (m, 3H), 3.17-3.23 (m, 1H), 3.07 (dd, J = 9.4, 5.9 Hz, 1H), 2.96 (dd, J = 13.3, 3.5 Hz, 1H), 2.39-2.49 (m, 2H, partially hidden by solvent peak) |
| 6 | 4-(((3S,4R)-1-((2-chloro-4-cyanophenyl)sulfonyl)-4-hydroxy-4-(hydroxymethyl)pyrrolidin-3-yl)methyl)-2-fluorobenzonitrile | 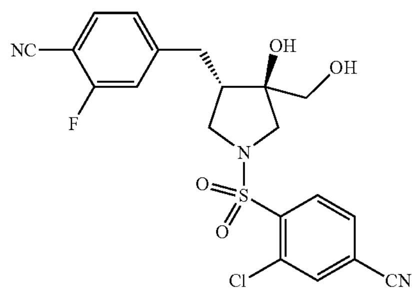 [SMILES: N#Cc1ccc(S(=O)(=O)N2C[C@H](Cc3ccc(C#N)c(F)c3)[C@](O)(CO)C2)c(Cl)c1] | 450.1 | $^1$H NMR (400 MHz, DMSO-$d_6$) δ: 8.36 (d, J = 1.5 Hz, 1H), 8.08-8.14 (m, 1H), 7.99-8.05 (m, 1H), 7.85 (t, J = 7.5 Hz, 1H), 7.30 (d, J = 10.5 Hz, 1H), 7.19 (dd, J = 8.0, 1.0 Hz, 1H), 5.18 (s, 1H), 4.91 (br., 1H), 3.63 (d, J = 10.0 Hz, 1H), 3.47 (d, J = 3.5 Hz, 2H), 3.40 (dd, J = 9.4, 6.4 Hz, 1H), 3.20 (d, J = 10.0 Hz, 1H), 3.07 (dd, J = 9.3, 5.5 Hz, 1H), 2.99 (d, J = 10.0 Hz, 1H), 2.40-2.50 (m, 2H, partially hidden by solvent peak) |

Example 7

4-(((3S,4S)-4-(aminomethyl)-1-((5-chloropyridin-2-yl)sulfonyl)-4-hydroxypyrrolidin-3-yl)methyl)-2-fluorobenzonitrile

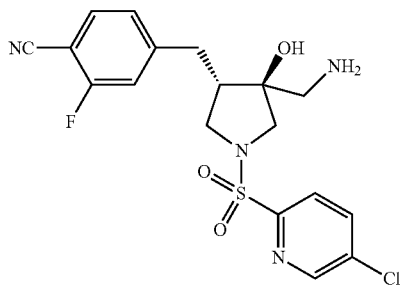 [SMILES: N#Cc1ccc(C[C@H]2CN(S(=O)(=O)c3ccc(Cl)cn3)C[C@@]2(O)CN)cc1F]

Step 1: N-allyl-N-(2-bromoallyl)-5-chloropyridine-2-sulfonamide

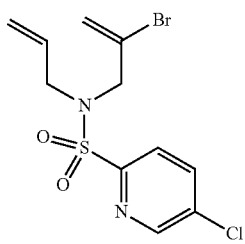 [SMILES: C=CCN(CC(=C)Br)S(=O)(=O)c1ccc(Cl)cn1]

To a suspension of K₂CO₃ (8.02 g, 58.0 mmol) in DMF (40 mL), was added prop-2-en-1-amine (1.4 mL, 18 mmol) followed by 5-chloropyridine-2-sulfonyl chloride (4.1 g, 19 mmol) and the mixture was stirred at rt for 1 h. 2,3-Dibromoprop-1-ene (2.1 mL, 21 mmol) was added and the reaction mixture was stirred at rt for 24 h. A second portion of 2,3-dibromoprop-1-ene (0.5 mL, 5.1 mmol) was added and the reaction mixture was again stirred 24 h. The reaction mixture was diluted with 50:50 EtOAc/hexanes, washed with H₂O (2×) and brine, dried over Na₂SO₄, filtered and concentrated under reduced pressure. The crude residue was purified by flash column chromatography (SiO₂) eluting with a gradient of 0-50% EtOAc in hexanes. The product fractions were combined and concentrated under reduced pressure to give the title compound as an oil (3.6 g, 53% yield). MS (m/z) 351.0 (M+H⁺).

Step 2: 4-((1-((5-chloropyridin-2-yl)sulfonyl)-4-methylenepyrrolidin-3-yl)methyl)-2-fluorobenzonitrile

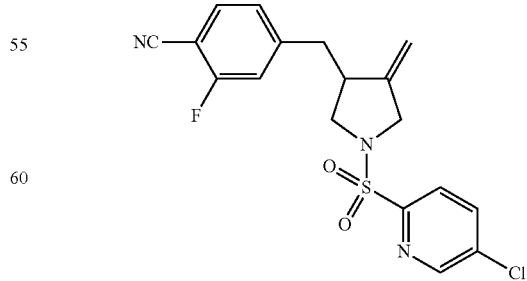

To a stirring suspension of N-allyl-N-(2-bromoallyl)-5-chloropyridine-2-sulfonamide (1.5 g, 4.2 mmol), Cs₂CO₃

(4.1 g, 13 mmol), and (4-cyano-3-fluorophenyl)boronic acid (0.70 g, 4.2 mmol) in THF (15 mL) and water (8 mL) was added PdCl$_2$(dppf) (0.31 g, 0.42 mmol). The mixture was purged with nitrogen and then heated at 60° C. for 45 min. The reaction mixture was cooled, diluted with EtOAc, washed with water (2×) and brine, dried over Na$_2$SO$_4$, filtered and concentrated under reduced pressure. The crude residue was purified by flash column chromatography (SiO$_2$) eluting with a gradient of 0-50% EtOAc in hexanes. The product fractions were pooled and concentrated under reduced pressure to afford the title compound as a viscous oil (0.746 g, (45% yield). MS (m/z) 392.0 (M+H$^+$).

Step 3: 4-(((3R,7S)-5-((5-chloropyridin-2-yl)sulfonyl)-1-oxa-5-azaspiro[2.4]heptan-7-yl)methyl)-2-fluorobenzonitrile

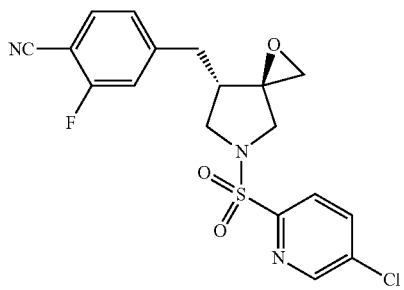 [SMILES: N#Cc1ccc(C[C@H]2CN(S(=O)(=O)c3ccc(Cl)cn3)C[C@@]23CO3)cc1F]

To a solution of 4-((1-((5-chloropyridin-2-yl)sulfonyl)-4-methylenepyrrolidin-3-yl)methyl)-2-fluorobenzonitrile (1.48 g, 3.78 mmol) in chloroform (25 mL) was added m-CPBA (2.54 g, 11.3 mmol) and the reaction mixture was stirred at rt for 24 h. The reaction mixture was diluted with DCM, washed with 10% Na$_2$S$_2$O$_3$ (aq), 10% NaHCO$_3$ (aq) and water. The organic layer was dried over Na$_2$SO$_4$, filtered and concentrated under reduced pressure to give a mixture of isomers as a white foam (1.48 g). Purification by chromatography (SFC, CC4 column, 30% IPA eluent) afforded the title compound as a white solid (267 mg, 17% yield). MS (m/z) 408.0 (M+H$^+$).

Step 4: 4-(((3S,4S)-4-(aminomethyl)-1-((5-chloropyridin-2-yl)sulfonyl)-4-hydroxypyrrolidin-3-yl)methyl)-2-fluorobenzonitrile To a solution of 4-(((3R,7S)-5-((5-chloropyridin-2-yl)sulfonyl)-1-oxa-5-azaspiro[2.4]heptan-7-yl)methyl)-2-fluorobenzonitrile (264 mg, 0.647 mmol) in methanol (2 mL) was added 2 M NH$_3$ in MeOH (11 mL, 22 mmol) and the mixture was subjected to microwave irradiation at 70° C. for 30 min. The pressure was carefully released and the solvent was evaporated under reduced pressure. The crude residue was purified by flash column chromatography (SiO$_2$) eluting with a gradient of 0-20% MeOH in DCM. The product fractions were pooled and concentrated under reduced pressure to give the title compound as a white foam (165 mg, 58% yield). $^1$H NMR (400 MHz, CD$_3$OD) δ: 8.74 (br s, 1H), 8.13 (d, J=8.3 Hz, 1H), 7.96 (d, J=8.5 Hz, 1H), 7.71 (t, J=7.3 Hz, 1H), 7.15-7.31 (m, 2H), 2.40-3.74 (m, 9H, partially hidden by solvent peak). MS (m/z) 425.2 (M+H$^+$).

Example 8—Capsule Composition

An oral dosage form for administering the present invention is produced by filing a standard two piece hard gelatin capsule with the ingredients in the proportions shown in Table 1, below.

TABLE 1

| INGREDIENTS | AMOUNTS |
| --- | --- |
| 4-(((3S,4R)-1-((2,4-dichlorophenyl)sulfonyl)-4-hydroxy-4-(hydroxymethyl)pyrrolidin-3-yl)methyl)-2-fluorobenzonitrile (Compound of Example 1) | 7 mg |
| Lactose | 53 mg |
| Talc | 16 mg |
| Magnesium Stearate | 4 mg |

Example 9—Injectable Parenteral Composition

An injectable form for administering the present invention is produced by stirring 1.7% by weight of 4-(((3S,4R)-1-((2-chloro-4-(trifluoromethyl)phenyl)sulfonyl)-4-hydroxy-4-(hydroxymethyl)pyrrolidin-3-yl)methyl)benzonitrile (Compound of Example 2) in 10% by volume propylene glycol in water.

Example 10 Tablet Composition

The sucrose, calcium sulfate dihydrate and a TRPV4 inhibitor as shown in Table 2 below, are mixed and granulated in the proportions shown with a 10% gelatin solution. The wet granules are screened, dried, mixed with the starch, talc and stearic acid, screened and compressed into a tablet.

TABLE 2

| INGREDIENTS | AMOUNTS |
| --- | --- |
| 4-(((3S,4R)-1-((5-chloropyridin-2-yl)sulfonyl)-4-hydroxy-4-(hydroxymethyl)pyrrolidin-3-yl)methyl)-3-(2,2,2-trifluoroethoxy)benzonitrile (Compound of Example 3) | 12 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:
1. A compound according to Formula I:

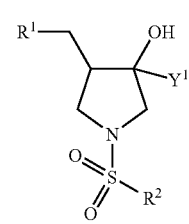

(I)

wherein:
R$^1$ is selected from:
  aryl,
  aryl substituted from 1 to 4 times by R$^a$,
  heteroaryl,
  heteroaryl substituted from 1 to 4 times by R$^a$,
  bicycloheteroaryl, and bicycloheteroaryl substituted from 1 to 4 times by R$^a$;

R$^2$ is selected from:
- aryl,
- aryl substituted from 1 to 4 times by R$^b$,
- heteroaryl,
- heteroaryl substituted from 1 to 4 times by R$^b$,
- bicycloheteroaryl, and
- bicycloheteroaryl substituted from 1 to 4 times by R$^b$, and Y$^1$ is selected from:
- C$_{1-6}$alkyl, and
- C$_{1-6}$alkyl substituted with from: 1 to 9 substitutents independently selected from:
  - fluoro,
  - chloro,
  - bromo,
  - iodo,
  - —OC$_{1-6}$alkyl,
  - —OC$_{1-6}$alkyl substituted with from 1 to 6 substituents independently selected from: fluoro, oxo, —OH, —COOH, —NH$_2$, and —CN,
  - mercapto,
  - —S(O)H,
  - —S(O)$_2$H,
  - oxo,
  - hydroxy,
  - amino,
  - —NHR$^{x11}$,
    where R$_{x11}$ is selected from C$_{1-6}$alkyl, and C$_{1-6}$alkyl substituted with from 1 to 6 substituents independently selected from: fluoro, oxo, —OH, —COOH, —NH$_2$, —CN, —OC$_{1-5}$alkyl, —OC$_{1-5}$alkyl substituted from 1 to 6 times by fluoro and —NH$_2$,
  - —NR$^{x12}$R$^{x13}$,
    where R$^{x12}$ and R$^{x13}$ are each independently selected from C$_{1-6}$alkyl, and C$_{1-6}$alkyl substituted with from 1 to 6 substituents independently selected from: fluoro, oxo, —OH, —COOH, —NH$_2$, and —CN,
  - —C(O)OH,
  - —C(O)NH$_2$,
  - aryl,
  - —Oaryl,
  - heteroaryl,
  - —Oheteroaryl,
  - —S(O)$_2$NH$_2$,
  - —NHS(O)$_2$H,
  - nitro, and
  - cyano, or Y$^1$ is taken together with the adjacent —OH to form a heterocyclic ring selected from:
- morpholinyl,
- morpholinyl substituted by —CH$_3$, and
- oxazolidin-2-one;

each R$^a$ is independently selected from:
- fluoro,
- chloro,
- bromo,
- iodo,
- —OH,
- C$_{1-6}$alkyl,
- C$_{1-6}$alkyl substituted with from 1 to 5 substituents independently selected from: fluoro, chloro, bromo, iodo, C$_{1-6}$alkyloxy, —OH, C$_{1-4}$alkyl, phenyl, oxo, —COOH, —NO$_2$, —NH$_2$ and —CN,
- cyano,
- —OC$_{1-6}$alkyl,
- —OC$_{1-6}$alkyl substituted with from 1 to 5 substituents independently selected from: fluoro, chloro, bromo, iodo, C$_{1-6}$alkyloxy, —OH, C$_{1-6}$alkyl, phenyl, oxo, —COOH, —NO$_2$, —NH$_2$ and —CN,
- —Ophenyl,
- —C(O)OC$_{1-6}$alkyl,
- —C(O)OC$_{1-6}$alkyl substituted 1 to 5 times by fluoro, and
- —Ocycloalkyl; and each R$^b$ is independently selected from:
- fluoro,
- chloro,
- bromo,
- iodo,
- —OH,
- C$_{1-6}$alkyl,
- C$_{1-6}$alkyl substituted with from 1 to 5 substituents independently selected from: fluoro, chloro, bromo, iodo, C$_{1-6}$alkyloxy, —OH, C$_{1-4}$alkyl, phenyl, oxo, —COOH, —NO$_2$, —NH$_2$ and —CN,
- cyano,
- —OC$_{1-6}$alkyl,
- —OC$_{1-6}$alkyl substituted with from 1 to 5 substituents independently selected from: fluoro, chloro, bromo, iodo, C$_{1-6}$alkyloxy, —OH, C$_{1-4}$alkyl, phenyl, oxo, —COOH, —NO$_2$, —NH$_2$ and —CN,
- phenyl,
- —C≡C—Si(CH$_3$)$_3$, and
- —C≡C-cycloalkyl;

or a pharmaceutically acceptable salt thereof.

2. The compound of claim 1 represented by the following Formula (II):

wherein:

R$^{21}$ is selected from:
- aryl,
- aryl substituted from 1 to 3 times by R$^{a2}$,
- heteroaryl, and
- heteroaryl substituted from 1 to 3 times by R$^{a2}$, R$^{22}$ is selected from:
- aryl,
- aryl substituted from 1 to 3 times by R$^{b2}$,
- heteroaryl, and
- heteroaryl substituted from 1 to 3 times by R$^{b2}$, and Y$^{21}$ is selected from:
- C$_{1-6}$alkyl, and
- C$_{1-6}$alkyl substituted with from: 1 to 9 substitutents independently selected from:
  - fluoro,
  - chloro,
  - bromo,
  - —OC$_{1-6}$alkyl, —OC$_{1-6}$alkyl substituted with from 1 to 6 substituents independently selected from: fluoro, oxo, —OH, —COOH, —NH$_2$, and —CN,
mercapto,
—S(O)H,
—S(O)$_2$H,
oxo,
hydroxy,
amino,
—NHR$^{x21}$,
where R$^{x21}$ is selected from C$_{1-5}$alkyl, and C$_{1-5}$alkyl substituted with from 1 to 6 substituents independently selected from: fluoro, oxo, —OH, —COOH, —NH$_2$, and —CN,
—C(O)OH,
—C(O)NH$_2$,
—S(O)$_2$NH$_2$,
—NHS(O)$_2$H,
nitro, and
cyano;
each R$^{a2}$ is independently selected from:
fluoro,
chloro,
bromo,
—OH,
C$_{1-6}$alkyl,
C$_{1-6}$alkyl substituted with from 1 to 5 substituents independently selected from: fluoro, chloro, bromo, iodo, C$_{1-4}$alkyloxy, —OH, C$_{1-6}$alkyl, phenyl, oxo, —COOH, —NO$_2$, —NH$_2$ and —CN,
cyano,
—OC$_{1-6}$alkyl,
—OC$_{1-6}$alkyl substituted with from 1 to 5 substituents independently selected from: fluoro, chloro, bromo, iodo, C$_{1-4}$alkyloxy, —OH, C$_{1-6}$alkyl, phenyl, oxo, —COOH, —NO$_2$, —NH$_2$ and —CN,
—Ophenyl,
—C(O)OC$_{1-6}$alkyl,
—C(O)OC$_{1-6}$alkyl substituted 1 to 5 times by fluoro, and
—Ocycloalkyl; and
each R$^{b2}$ is independently selected from:
fluoro,
chloro,
bromo,
—OH,
C$_{1-6}$alkyl,
C$_{1-6}$alkyl substituted with from 1 to 5 substituents independently selected from: fluoro, chloro, bromo, iodo, C$_{1-4}$alkyloxy, —OH, C$_{1-6}$alkyl, phenyl, oxo, —COOH, —NO$_2$, —NH$_2$ and —CN,
cyano,
—OC$_{1-6}$alkyl,
—OC$_{1-6}$alkyl substituted with from 1 to 5 substituents independently selected from: fluoro, chloro, bromo, iodo, C$_{1-4}$alkyloxy, —OH, C$_{1-6}$alkyl, phenyl, oxo, —COOH, —NO$_2$, —NH$_2$ and —CN,
and
phenyl;
or a pharmaceutically acceptable salt thereof.

3. The compound of claim 1 represented by the following Formula (III):

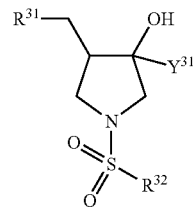

(III)

wherein:
R$^{31}$ is selected from:
phenyl,
phenyl substituted from 1 to 3 times by R$^{a3}$,
pyrimidine,
pyrimidine substituted from 1 to 3 times by R$^{a3}$,
pyridine, and
pyridine substituted from 1 to 3 times by R$^{a3}$;
R$^{32}$ is selected from:
phenyl,
phenyl substituted from 1 to 3 times by R$^{b3}$,
pyridine,
pyridine substituted from 1 to 3 times by R$^{b3}$,
pyrimidine,
pyrimidine substituted from 1 to 3 times by R$^{b3}$,
pyridazine, and
pyridazine substituted from 1 to 3 times by R$^{b3}$; and
Y$^{31}$ is selected from:
—CH$_2$OH,
—CH(OH)CH$_3$,
—CH(OH)CH$_2$CH$_3$,
—C(OH)(CH$_3$)$_2$,
—CH$_2$NH$_2$,
—CH$_2$NHR$^{x30}$, and
—CH(NH$_2$)CH$_3$;
where each R$^{x30}$ is independently selected from: C$_{1-6}$alkyl, and C$_{1-6}$alkyl substituted with from 1 to 6 substituents independently selected from: fluoro, oxo, —OH, —COOH, —NH$_2$, and —CN;
each R$^{a3}$ is independently selected from:
fluoro,
chloro,
bromo,
—OH,
C$_{1-6}$alkyl,
cyano,
—CF$_3$,
C$_{1-6}$alkylCF$_3$,
—CHF$_2$,
—CH$_2$F,
—OC$_{1-5}$alkyl,
—OCF$_3$,
—O$_{1-4}$alkylCF$_3$,
C$_{1-6}$alkylCN,
—C(O)OC$_{1-3}$alkyl,
—C(O)OH, and
Ocycloalkyl; and
each R$^{b3}$ is independently selected from:
fluoro,
chloro,
bromo,
—OH,
C$_{1-6}$alkyl,
cyano, —CF$_3$,
—C$_{1-6}$alkylCF$_3$,
—CHF$_2$,
—CH$_2$F,
—OC$_{1-3}$alkyl,
—OCF$_3$,
—OC$_{1-6}$alkylCF$_3$,
—C(O)CH$_3$, and
—OCHF$_2$;
or a pharmaceutically acceptable salt thereof.

4. The compound of claim 1 represented by the following Formula (IV):

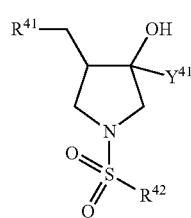

(IV)

wherein:
R$^{41}$ is selected from:
phenyl, and
phenyl substituted from 1 to 3 times by R$^{a4}$;
R$^{42}$ is selected from:
phenyl,
phenyl substituted from 1 to 3 times by R$^{b4}$,
pyridine, and
pyridine substituted from 1 to 3 times by R$^{b4}$; and
Y$^{41}$ is selected from:
—CH$_2$OH,
—CH$_2$NH$_2$, and
—CH$_2$NHR$^{x40}$;
where each R$^{x40}$ is independently selected from: C$_{1-6}$alkyl, and C$_{1-6}$alkyl substituted with from 1 to 6 substituents independently selected from: fluoro, oxo, —OH, —COOH, —NH$_2$, and —CN;
each R$^{a4}$ is independently selected from:
fluoro,
chloro,
bromo,
—OH,
C$_{1-6}$alkyl,
cyano,
—CF$_3$,
—CHF$_2$,
—CH$_2$F,
—OC$_{1-3}$alkyl,
—OCF$_3$,
—C(O)OC$_{1-3}$alkyl, and
—C(O)OH, and
each R$^{b4}$ is independently selected from:
fluoro,
chloro,
—OH,
C$_{1-6}$alkyl,
cyano,
—CF$_3$,
—CHF$_2$,
—CH$_2$F,
—OC$_{1-3}$alkyl,
—OCF$_3$,
—C(O)CH$_3$, and
—OCHF$_2$; and
or a pharmaceutically acceptable salt thereof.

5. A compound of claim 1 selected from:
4-(((3S,4R)-1-((2,4-dichlorophenyl)sulfonyl)-4-hydroxy-4-(hydroxymethyl)pyrrolidin-3-yl) methyl)-2-fluorobenzonitrile;
4-(((3S,4R)-1-((2-chloro-4-(trifluoromethyl)phenyl)sulfonyl)-4-hydroxy-4-(hydroxymethyl)pyrrolidin-3-yl) methyl)benzonitrile;
4-(((3S,4R)-1-((5-chloropyridin-2-yl)sulfonyl)-4-hydroxy-4-(hydroxymethyl) pyrrolidin-3-yl) methyl)-3-(2,2,2-trifluoroethoxy)benzonitrile;
4-(((3S,4S)-1-((2,4-dichlorophenyl)sulfonyl)-4-hydroxy-4-(hydroxymethyl) pyrrolidin-3-yl)methyl)-2-fluorobenzonitrile;
4-(((3S,4R)-1-((2-cyano-4-(trifluoromethyl)phenyl)sulfonyl)-4-hydroxy-4-(hydroxymethyl)pyrrolidin-3-yl) methyl)-2-fluorobenzonitrile;
4-(((3S,4R)-1-((2-chloro-4-cyanophenyl)sulfonyl)-4-hydroxy-4-(hydroxymethyl) pyrrolidin-3-yl)methyl)-2-fluorobenzonitrile;
4-(((3S,4S)-4-(aminomethyl)-1-((5-chloropyridin-2-yl) sulfonyl)-4-hydroxypyrrolidin-3-yl)methyl)-2-fluorobenzonitrile;
or a pharmaceutically acceptable salt thereof.

6. A pharmaceutical composition comprising a compound of Formula (I) according to claim 1 or a pharmaceutically acceptable salt thereof and a pharmaceutically acceptable excipient.

7. A method of treating a disease state selected from: atherosclerosis, related dysfunctions and congestive heart failure, pulmonary disorder, ventilator induced lung injury, high altitude induced pulmonary edema, acute respiratory distress syndrome, acute lung injury, pain, in a human in need thereof, which comprises administering to such human a safe and effective amount of a compound according to Formula (I) of claim 1, or a pharmaceutically acceptable salt thereof.

8. A method according to claim 7 wherein the compound or pharmaceutically acceptable salt thereof is administered orally.

9. A method according to claim 7 wherein the compound or pharmaceutically acceptable salt thereof is administered intravenously.

10. A method according to claim 7 wherein the compound or pharmaceutically acceptable salt thereof is administered by inhalation.

11. A method according to claim 7 wherein the disease state is acute lung injury.

12. A method according to claim 7 wherein the disease state is heart failure.

13. A method according to claim 7 wherein the disease state is acute respiratory distress syndrome.

14. A method of treating a disease state selected from heart failure, in a human in need thereof, which comprises administering to such human a safe and effective amount of a compound according to Formula (I) of claim 1, or a pharmaceutically acceptable salt thereof.

15. A method according to claim 7 wherein the disease state is acute cough.

16. A method according to claim 7 wherein the disease state is sub-acute cough.

17. A method according to claim 7 wherein the disease state is chronic cough.

18. The method of inhibiting TRPV4 activity in a human in need thereof, which comprises administering to such human a safe and effective amount of a compound according to Formula (I) of claim 1, or a pharmaceutically acceptable salt thereof.

19. A method of treating a disease state in a human in need thereof according to claim 7, which comprises administering to such human a safe and effective amount of
  a) a compound according to Formula (I), of claim 1 or a pharmaceutically acceptable salt thereof; and
  b) at least one agent selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blockers, aldosterone antagonists, inotropes, NSAIDS, nitric oxide donors, calcium channel modulators, muscarinic antagonists, steroidal anti-inflammatory drugs, bronchodilators, antihistamines, leukotriene antagonists, HMG-CoA reductase inhibitors, dual non-selective β-adrenoceptor and α1-adrenoceptor antagonists, type-5 phosphodiesterase inhibitors, and renin inhibitors.

20. A process for preparing a pharmaceutical composition containing a pharmaceutically acceptable excipient and an effective amount of a compound according to Formula (I) of claim 1 or a pharmaceutically acceptable salt thereof, which process comprises bringing the compound of Formula (I) or a pharmaceutically acceptable salt thereof into association with a pharmaceutically acceptable excipient.

\* \* \* \* \*